United States Patent
Maharaj et al.

(10) Patent No.: US 10,201,457 B2
(45) Date of Patent: Feb. 12, 2019

(54) WOUND PACKING DEVICE WITH NANOTEXTURED SURFACE

(71) Applicant: SurModics, Inc., Eden Prairie, MN (US)

(72) Inventors: Gary Maharaj, Eden Prairie, MN (US); Teryl L. Woodwick Sides, Maple Grove, MN (US)

(73) Assignee: Surmodics, Inc., Eden Prairie, MN (US)

( * ) Notice: Subject to any disclaimer, the term of this patent is extended or adjusted under 35 U.S.C. 154(b) by 602 days.

(21) Appl. No.: 14/813,928

(22) Filed: Jul. 30, 2015

(65) Prior Publication Data
US 2016/0030254 A1 Feb. 4, 2016

Related U.S. Application Data

(60) Provisional application No. 62/032,244, filed on Aug. 1, 2014.

(51) Int. Cl.
*A61F 13/00* (2006.01)

(52) U.S. Cl.
CPC .. *A61F 13/00072* (2013.01); *A61F 13/00063* (2013.01); *A61F 13/00987* (2013.01); *A61F 2013/0054* (2013.01); *A61F 2013/00557* (2013.01)

(58) Field of Classification Search
CPC .......... A61F 13/00021; A61F 13/00029; A61F 13/00042; A61F 13/00063; A61F 2013/0054; A61F 2013/00553; A61F 2013/00557
See application file for complete search history.

(56) References Cited

U.S. PATENT DOCUMENTS

| | | |
|---|---|---|
| 457,390 A | 8/1891 | Weeks |
| 3,030,951 A | 4/1962 | Mandarino |
| 3,095,877 A | 7/1963 | Rowan |
| 3,882,858 A | 5/1975 | Klemm |
| 3,915,955 A | 10/1975 | Cooper et al. |
| 3,965,905 A | 6/1976 | Schoenholz et al. |
| 3,987,497 A | 10/1976 | Stoy et al. |

(Continued)

FOREIGN PATENT DOCUMENTS

| | | |
|---|---|---|
| CN | 1048157 | 1/1991 |
| DE | 3037270 | 5/1982 |

(Continued)

OTHER PUBLICATIONS

"Communication Pursuant to Article 94(3) EPC," for European Patent Application No. 13783782.9 dated Jun. 2, 2017 (3 pages).

(Continued)

*Primary Examiner* — Lynne Anderson
(74) *Attorney, Agent, or Firm* — Pauly, DeVries Smith & Deffner LLC

(57) ABSTRACT

Embodiments of the invention include wound packing devices and methods of making and using the same. In an embodiment, the invention includes a wound packing device including a plurality of spacing elements comprising a nanotextured surface. The wound packing device can also include a connector connecting the plurality of spacing elements to one another. Other embodiments are also included herein.

4 Claims, 13 Drawing Sheets

(56) References Cited

U.S. PATENT DOCUMENTS

| | | |
|---|---|---|
| 4,036,622 A | 7/1977 | Carroll et al. |
| 4,059,684 A | 11/1977 | Gross et al. |
| 4,191,740 A | 3/1980 | Heusser et al. |
| 4,191,743 A | 3/1980 | Klemm et al. |
| 4,233,287 A | 11/1980 | Heusser et al. |
| 4,329,743 A | 5/1982 | Alexander et al. |
| 4,347,841 A | 9/1982 | Benyo et al. |
| 4,373,217 A | 2/1983 | Draenert |
| 4,373,519 A | 2/1983 | Errede et al. |
| 4,440,750 A | 4/1984 | Glowacki et al. |
| 4,456,711 A | 6/1984 | Pietsch et al. |
| 4,460,642 A | 7/1984 | Errede et al. |
| 4,500,658 A | 2/1985 | Fox |
| 4,535,485 A | 8/1985 | Ashman et al. |
| 4,547,390 A | 10/1985 | Ashman et al. |
| 4,563,489 A | 1/1986 | Urist |
| 4,563,502 A | 1/1986 | Liu |
| 4,575,539 A | 3/1986 | Decrosta et al. |
| 4,613,502 A | 9/1986 | Turkova et al. |
| 4,619,655 A | 10/1986 | Hanker et al. |
| 4,791,150 A | 12/1988 | Braden et al. |
| 4,837,285 A | 6/1989 | Berg et al. |
| 4,853,225 A | 8/1989 | Wahlig et al. |
| 4,863,444 A | 9/1989 | Blomer |
| 4,881,546 A | 11/1989 | Kaessmann |
| 4,892,516 A | 1/1990 | Harle |
| 4,900,546 A | 2/1990 | Posey-Dowty et al. |
| 4,916,193 A | 4/1990 | Tang |
| 4,933,034 A | 6/1990 | Kokubu et al. |
| 4,960,415 A | 10/1990 | Reinmuller et al. |
| 4,963,151 A | 10/1990 | Ducheyne et al. |
| 4,968,539 A | 11/1990 | Aoyagi et al. |
| 4,994,071 A | 2/1991 | Macgregor |
| 5,002,582 A | 3/1991 | Guire et al. |
| 5,031,608 A | 7/1991 | Weinstein |
| 5,037,445 A | 8/1991 | Sander et al. |
| 5,055,307 A | 10/1991 | Tsuru et al. |
| 5,073,373 A | 12/1991 | O'leary et al. |
| 5,100,490 A | 3/1992 | Holroyd et al. |
| 5,106,614 A | 4/1992 | Posey-Dowty et al. |
| 5,114,512 A | 5/1992 | Holroyd et al. |
| 5,154,951 A | 10/1992 | Finnicum et al. |
| 5,156,961 A | 10/1992 | Ioue et al. |
| 5,164,036 A | 11/1992 | Abe |
| 5,190,748 A | 3/1993 | Bachynsky et al. |
| 5,221,698 A | 6/1993 | Amidon et al. |
| 5,248,732 A | 9/1993 | Drzewinski |
| 5,258,291 A | 11/1993 | Inoue et al. |
| 5,268,178 A | 12/1993 | Calhoun et al. |
| 5,281,419 A | 1/1994 | Tuan |
| 5,304,121 A | 4/1994 | Sahatjian |
| 5,328,533 A | 7/1994 | Yasuno et al. |
| 5,334,626 A | 8/1994 | Lin |
| 5,344,452 A | 9/1994 | Lemperle et al. |
| 5,414,075 A | 5/1995 | Swan et al. |
| 5,447,505 A | 9/1995 | Valentine et al. |
| 5,464,650 A | 11/1995 | Berg et al. |
| 5,470,625 A | 11/1995 | Perrault |
| 5,486,593 A | 1/1996 | Tang et al. |
| 5,487,899 A | 1/1996 | Davis |
| 5,512,610 A | 4/1996 | Lin |
| 5,556,703 A | 9/1996 | Gross et al. |
| 5,582,838 A | 12/1996 | Rork et al. |
| 5,624,411 A | 4/1997 | Tuch |
| 5,629,009 A | 5/1997 | Laurencin et al. |
| 5,637,460 A | 6/1997 | Swan et al. |
| 5,641,514 A | 6/1997 | Cho |
| 5,665,109 A | 9/1997 | Yoon |
| 5,667,501 A | 9/1997 | Fowler et al. |
| 5,714,360 A | 2/1998 | Swan et al. |
| 5,714,577 A | 2/1998 | Montelaro et al. |
| 5,716,337 A | 2/1998 | Mccabe et al. |
| 5,733,545 A | 3/1998 | Hood, III |
| 5,749,602 A | 5/1998 | Delaney et al. |
| 5,755,706 A | 5/1998 | Kronenthal et al. |
| 5,755,787 A | 5/1998 | Camprasse et al. |
| 5,756,127 A | 5/1998 | Grisoni et al. |
| 5,833,642 A | 11/1998 | Mccabe et al. |
| 5,859,150 A | 1/1999 | Jamiolkowski et al. |
| 5,882,858 A | 3/1999 | Dalla-Favera et al. |
| 5,902,839 A | 5/1999 | Lautenschlager et al. |
| 5,906,205 A | 5/1999 | Hiebert |
| 5,919,477 A | 7/1999 | Bevan et al. |
| 5,935,595 A | 8/1999 | Steen |
| 5,945,507 A | 8/1999 | Montelaro et al. |
| 5,958,465 A | 9/1999 | Klemm et al. |
| 5,972,366 A | 10/1999 | Haynes et al. |
| 6,007,833 A | 12/1999 | Chudzik et al. |
| 6,020,396 A | 2/2000 | Jacobs |
| 6,077,698 A | 6/2000 | Swan et al. |
| 6,106,495 A | 8/2000 | Scott et al. |
| 6,110,483 A | 8/2000 | Whitbourne et al. |
| 6,156,330 A | 12/2000 | Tsukada et al. |
| 6,197,330 B1 | 3/2001 | Rees et al. |
| 6,214,901 B1 | 4/2001 | Chudzik et al. |
| 6,242,995 B1 | 6/2001 | Shikama et al. |
| 6,264,780 B1 | 7/2001 | Iwanaga et al. |
| 6,299,898 B2 | 10/2001 | Rees et al. |
| 6,309,669 B1 | 10/2001 | Setterstrom et al. |
| 6,344,035 B1 | 2/2002 | Chudzik et al. |
| 6,355,705 B1 | 3/2002 | Bond et al. |
| 6,361,731 B1 | 3/2002 | Smith et al. |
| 6,391,336 B1 | 5/2002 | Royer |
| 6,413,342 B1 | 7/2002 | Yun et al. |
| 6,413,539 B1 | 7/2002 | Shalaby |
| 6,492,471 B1 | 12/2002 | Eisenbeiss et al. |
| 6,495,127 B1 | 12/2002 | Wallace et al. |
| 6,500,861 B1 | 12/2002 | Wider |
| 6,503,267 B2 | 1/2003 | Bonutti et al. |
| 6,503,539 B2 | 1/2003 | Gestrelius et al. |
| 6,530,934 B1 | 3/2003 | Jacobsen et al. |
| 6,531,146 B2 | 3/2003 | Calhoun et al. |
| 6,576,263 B2 | 6/2003 | Truong et al. |
| 6,579,533 B1 | 6/2003 | Tormala et al. |
| 6,582,696 B2 | 6/2003 | Kuri-Harcuch et al. |
| 6,582,713 B2 | 6/2003 | Newell et al. |
| 6,630,486 B1 | 10/2003 | Royer et al. |
| 6,656,488 B2 | 12/2003 | Yi et al. |
| 6,673,362 B2 | 1/2004 | Calhoun et al. |
| 6,689,153 B1 | 2/2004 | Skiba |
| 6,692,510 B2 | 2/2004 | West |
| 6,700,032 B1 | 3/2004 | Gray |
| 6,713,083 B1 | 3/2004 | Mcgregor et al. |
| 6,720,009 B2 | 4/2004 | Gtestrelius et al. |
| 6,835,713 B2 | 12/2004 | Montelaro et al. |
| 6,844,010 B1 | 1/2005 | Friden et al. |
| 6,869,976 B2 | 3/2005 | Royer |
| 6,887,847 B2 | 5/2005 | Montelaro et al. |
| 6,890,583 B2 | 5/2005 | Chudzik et al. |
| 6,902,743 B1 | 6/2005 | Setterstrom et al. |
| 6,908,065 B1 | 6/2005 | Ritchie |
| 6,942,877 B2 | 9/2005 | Vogt et al. |
| 6,979,324 B2 | 12/2005 | Bybordi et al. |
| 6,998,510 B2 | 2/2006 | Buckman et al. |
| 7,008,667 B2 | 3/2006 | Chudzik et al. |
| 7,070,609 B2 | 7/2006 | West |
| 7,097,850 B2 | 8/2006 | Chappa et al. |
| 7,131,997 B2 | 11/2006 | Bourne et al. |
| 7,547,445 B2 | 6/2009 | Chudzik et al. |
| 7,807,750 B2 | 10/2010 | Taton et al. |
| 8,512,736 B2 | 8/2013 | Chudzik et al. |
| 8,685,421 B2 | 4/2014 | Kloke et al. |
| 8,697,106 B2 | 4/2014 | Kloke et al. |
| 8,815,259 B2 * | 8/2014 | Taton ............ A61L 27/34 424/400 |
| 8,889,760 B2 | 11/2014 | Kurdyumov et al. |
| 8,900,217 B2 | 12/2014 | Malhi |
| 9,155,671 B2 | 10/2015 | Fuller et al. |
| 2001/0001039 A1 | 5/2001 | Rees et al. |
| 2002/0001609 A1 | 1/2002 | Calhoun et al. |
| 2002/0018795 A1 | 2/2002 | Whitbourne et al. |
| 2002/0172709 A1 | 11/2002 | Nielsen et al. |
| 2002/0183265 A1 | 12/2002 | Vogt et al. |
| 2002/0192191 A1 | 12/2002 | Kuri-Harcuch et al. |

(56) References Cited

U.S. PATENT DOCUMENTS

| | | |
|---|---|---|
| 2004/0009228 A1 | 1/2004 | Tormala et al. |
| 2004/0033251 A1 | 2/2004 | Sparer et al. |
| 2004/0047891 A1 | 3/2004 | Glozman et al. |
| 2004/0105880 A1 | 6/2004 | Turner et al. |
| 2004/0115273 A1 | 6/2004 | Sparer et al. |
| 2004/0116511 A1 | 6/2004 | Malik |
| 2004/0121290 A1 | 6/2004 | Minevski et al. |
| 2004/0127978 A1 | 7/2004 | Sparer et al. |
| 2004/0193187 A1 | 9/2004 | Boehringer et al. |
| 2004/0208934 A1 | 10/2004 | Royer |
| 2004/0247644 A1 | 12/2004 | Bratt et al. |
| 2004/0259949 A1 | 12/2004 | Klaveness et al. |
| 2004/0265371 A1 | 12/2004 | Looney et al. |
| 2005/0058767 A1 | 3/2005 | Bolton et al. |
| 2005/0064009 A1 | 3/2005 | Bates |
| 2005/0070835 A1 | 3/2005 | Joshi |
| 2005/0145320 A1 | 7/2005 | Niwa |
| 2005/0208134 A1 | 9/2005 | Magdassi et al. |
| 2005/0218541 A1 | 10/2005 | Peng et al. |
| 2005/0233475 A1 | 10/2005 | Wang et al. |
| 2005/0241535 A1 | 11/2005 | Bohner |
| 2005/0260246 A1 | 11/2005 | Chudzik et al. |
| 2005/0271604 A1 | 12/2005 | Gestrelius et al. |
| 2005/0281858 A1 | 12/2005 | Kloke et al. |
| 2006/0024357 A1 | 2/2006 | Carpenter et al. |
| 2006/0029637 A1 | 2/2006 | Tice et al. |
| 2006/0030669 A1 | 2/2006 | Taton et al. |
| 2006/0057224 A1 | 3/2006 | Hynes |
| 2006/0105031 A1 | 5/2006 | Bolton et al. |
| 2006/0106967 A1 | 5/2006 | Brocco et al. |
| 2006/0188486 A1 | 8/2006 | Carpenter et al. |
| 2006/0240072 A1 | 10/2006 | Chudzik et al. |
| 2007/0010775 A1 | 1/2007 | Lutri |
| 2007/0016163 A1 | 1/2007 | Santini, Jr. et al. |
| 2007/0026037 A1 | 2/2007 | Kloke et al. |
| 2007/0026052 A1 | 2/2007 | Baggett |
| 2007/0048350 A1 | 3/2007 | Falotico et al. |
| 2007/0077280 A1 | 4/2007 | Collinge et al. |
| 2007/0088370 A1 | 4/2007 | Kahle et al. |
| 2007/0185463 A1* | 8/2007 | Mulligan ............ A61F 13/0203 604/305 |
| 2008/0188819 A1 | 8/2008 | Kloke et al. |
| 2009/0202609 A1 | 8/2009 | Keough et al. |
| 2009/0312725 A1 | 12/2009 | Braga |
| 2010/0292549 A1* | 11/2010 | Shuler ................. A61B 5/0215 600/324 |
| 2010/0324510 A1 | 12/2010 | Andresen et al. |
| 2011/0112492 A1 | 5/2011 | Bharti et al. |
| 2011/0213319 A1 | 9/2011 | Blott et al. |
| 2012/0021038 A1 | 1/2012 | Kloke et al. |
| 2012/0046384 A2 | 2/2012 | Kurdyumov et al. |
| 2013/0143056 A1 | 6/2013 | Swan et al. |
| 2013/0199539 A1 | 8/2013 | Webster et al. |
| 2014/0180229 A1 | 6/2014 | Fuller et al. |
| 2014/0364819 A1* | 12/2014 | VanDelden ....... A61F 13/00021 604/290 |
| 2015/0148760 A1 | 5/2015 | Dodd et al. |
| 2016/0022502 A1 | 1/2016 | Fuller et al. |

FOREIGN PATENT DOCUMENTS

| | | |
|---|---|---|
| DE | 3127696 | 2/1983 |
| EP | 0157909 | 10/1985 |
| EP | 0575090 | 12/1993 |
| EP | 0852148 | 7/1998 |
| EP | 0888785 | 1/1999 |
| EP | 1340476 | 9/2003 |
| EP | 1493451 | 1/2005 |
| EP | 1265550 | 5/2005 |
| EP | 1588675 | 10/2005 |
| EP | 1745806 | 1/2007 |
| EP | 2908870 | 5/2018 |
| FR | 2757528 | 6/1998 |
| GB | 2376632 | 12/2002 |
| JP | 5361188 | 6/1978 |
| JP | 5393687 | 8/1978 |
| JP | 57004915 | 1/1982 |
| JP | 60156468 | 8/1985 |
| JP | 01-093444 | 4/1989 |
| JP | 04-189352 | 7/1992 |
| JP | 05-078233 | 3/1993 |
| JP | 05-305134 | 11/1993 |
| JP | 06-178801 | 6/1994 |
| JP | 07-017851 | 1/1995 |
| JP | 07-039578 | 2/1995 |
| JP | 07-227171 | 8/1995 |
| JP | 07-308374 | 11/1995 |
| JP | 9262278 | 10/1997 |
| JP | 10-045608 | 2/1998 |
| JP | 63103809 | 5/1998 |
| JP | 10-158075 | 6/1998 |
| JP | 11-029374 | 2/1999 |
| JP | 11-076293 | 3/1999 |
| JP | 2002165827 | 6/2002 |
| JP | 2002-249373 | 9/2002 |
| JP | 2003062057 | 3/2003 |
| JP | 2005015484 | 1/2005 |
| KR | 20000040011 | 7/2000 |
| KR | 20020041927 | 6/2002 |
| WO | 8203174 | 9/1982 |
| WO | 9301841 | 2/1993 |
| WO | 0024378 | 5/2000 |
| WO | 02067849 | 9/2002 |
| WO | 03070135 | 8/2003 |
| WO | 2004022000 | 3/2004 |
| WO | 2005007077 | 1/2005 |
| WO | 2006005939 | 1/2006 |
| WO | 2006031965 | 3/2006 |
| WO | 2006119256 | 11/2006 |
| WO | 2007016405 | 2/2007 |
| WO | 2007027849 | 3/2007 |
| WO | 2008006083 | 1/2008 |
| WO | 2008135551 | 11/2008 |
| WO | 2010017437 | 2/2010 |
| WO | 2010075180 | 7/2010 |
| WO | 2014062839 | 4/2014 |
| WO | 2016019279 | 2/2016 |

OTHER PUBLICATIONS

"Office Action," for Japanese Patent Application No. 2015-537800 dated Jul. 18, 2017 (10 pages) with English translation.

"Response to Communication Pursuant to Article 94(3) EPC," for European Patent Application No. 13783782.9, filed with the EPO Apr. 28, 2017 (6 pages).

"Response to Communication Pursuant to Article 94(3) EPC," for European Patent Application No. 13783782.9, filed with the EPO Sep. 26, 2017 (42 pages).

Adams, Kenneth et al., "In Vitro and In Vivo Evaluation of Antibiotic Diffusion from Antibiotic-Impregnated Polymethylmethacrylate Beads," Clinical Orthopaedics and Related Research, No. 278 (1992), pp. 244-252.

Alpern, Eytan J. "In Vitro Elution Characteristics of Tobramycin and Vancomycin Release from Locally Implantable Biodegradable Sponges," Market Research, an Alternate Technology, htto://www.hwbf.org/ota/am/ota99/otapo/OTP99029.htm (2006), 2 pages.

Alpert, Brian et al., "The In Vivo Behavior of Gentamicin-PMMA Beads in the Maxillofacial Region," J. Oral Maxillofac. Surg., vol. 47 (1989), pp. 46-49.

Bayston, R. "The Sustained Release of Antimicrobial Drugs from Bone Cement," J. Bone Joint Surg, 64-B:460 (1982), pp. 460-464.

Black, John L. et al., "Military Service: A Mayo Clinic tradition," Mayo Alumni, Spring 2006, pp. 2-7.

Blaha, J. D. et al., "Comparison of the Clinical Efficacy and Tolerance of Gentamicin PMMA Beads on Surgical Wire Versus Combined and Systemic Therapy for Osteomyelitis," Clin Orthop Relat Res. (295):8-12 (Abstract Only), 1983, 1 page.

Bowyer, G. W. "Antibiotic Impregnated Beads in Open Fractures," J R Army Medical Corps, 139(3)100-4.Links, (1993), abstract only, 2 pages.

(56) References Cited

OTHER PUBLICATIONS

Bowyer, Gavin W. et al., "Antibiotic Release from Impregnated Pellets and Beads," The Journal of Trauma, vol. 36, No. 3 (1994), pp. 331-335.

Buranapanitkit, Boonsin et al., "In Vitro Inhibitive Effect of Antibiotic Beads to Common Orthopaedic Pathogens: Home-made vs. Commercial Beads," The Thai J of Orthop Surg, 25(2): 48-52, Abstract, http://medinfo.psu.ac.th/AnnualResearch/2000/bboo1.htm (2000), 1 page.

Burd, Timothy A. et al., "In Vitro Elution of Tobramycin From Bioabsorbable Polycaprolactone Beads," Journal of Orthopaedic Trauma, vol. 15, No. 6 (2001), pp. 424-428.

Butson, R. J. et al., "Treatment of Intrasynovial Infection with Gentamicin-impregnated Polymethylmethacrylate Beads," The Veterinary Record, No. 138 (1996), pp. 460-464.

Calhoun, Jason H. et al., "Antibiotic Beads in the Management of Surgical Infections," The American Journal of Surgery, vol. 157 (1989), pp. 443-449.

Calhoun, Jason H. et al., "The Treatment of Infected Nonunions with Gentamicin-Polymethylmethacrylate Antibiotic Beads," Clinical Orthopaedics and Related Research, No. 295 (1993), pp. 23-27.

Calhoun, M.D., Jason "Antibiotics and War Wounds," Extremity War Injuries; State of the Art and Future Directions, Presentation Abstracts, Session III: Antibiotics and Infections: Moderator's Overview, 14, date unknown, 1 page.

Campoccia, Davide et al., "The Significance of Infection Related to Orthopedic Devices and Issues of an Antibiotic Resistance," Biomaterials 27 (2006), pp. 2331-2339.

Cassas, M.D., Kyle J. et al., "Childhood and Adolescent Sports-Related Overuse Injuries," American Family Physicians, vol. 73, No. 6 (2006), pp. 1014-1022.

Celikoz, B. et al., "Subacute Reconstruction of Lower Leg and Foot Defects Due to High Velocity-High Energy Injuries Caused by Gunshots, Missiles, and Land Mines," Microsurgery: 25(1) :3-14; discussion 15, Abstract from www.pubmed.gov (2005), 2 pages.

Cierny, Iii, George et al., "Treatment of Chronic Infection," J Am Acad Orthop Surg, vol. 14, No. 10, 2006, (9 pages).

Clasper, J. "The Interaction of Projectiles with Tissues and the Management of Ballistic Fractures," J R Army Med Corps; 147(1):52-61, Abstract, from www.pubmed.gov (2011), 1 page.

"Communication Pursuant to Rules 161(1) and 162 EPC," for European Application No. 13783782.9, dated Jun. 18, 2015 (2 pages).

"Controversies in the Treatment of Open Tibial Fractures," Advances in the Treatment of Tibial Shaft Fractures: A Current Concepts Review, Medscape Portals, Inc. (2000) 4 pages.

Covey, M.D., Dana C. "Combat Orthopaedics: A View from the Trenches," J Am Acad Orthop Surg, vol. 14, No. 10, 2006, (11 pages).

Cunningham, Amy et al., "Antibiotic Bead Production," Iowa Orthopaedic J, 20:31-35 (2000), pp. 31-35.

Davis, Kepler A. et al., "Multidrug-Resistant Acinetobacter Extremity Infections in Soldiers," Emerging Infectious Diseases, www.cdc.gov/eid, vol. 1. No. 8, Aug. 2005, pp. 1218-1224.

Decoster, M.D., Thomas A. et al., "Preparation and Use of Antibiotic-Impregnated Beads for Orthopaedic Infections," Abstract only, date not known, 1 page.

Deslouches, B. et al., "Activity of the De Novo Engineered Antimicrobial Peptide WLBU2 Against Pseudomonas Aeruginosa in Human Serum and Whole Blood: Implications for Systemic Applications," J. Antimicrobial Agents & Chemotherapy, 49(8): (2005) pp. 3208-3216.

Dierks, Eric J. et al., "Treatment of an Infected Mandibular Graft Using Tobramycin-Impregnated Methylmethacrylate Beads: Report of a Case," Journal of Oral and Maxillofacial Surgery, vol. 50, No. 11, 1992, (4 pages).

Dullea, Mark "C-077R Markets for Advanced Wound Care Technologies," http://www.bccresearch.com/biotech/C0774.html, May 1, 2006, pp. 1-16.

Eckman, Jr., James B. et al., "Wound and Serum Levels of Tobramycin With the Prophylactic Use of Tobramycin-Impregnated Polymethylmethacrylate Beads in Compound Fractures," Clinical Orthopaedics and Related Research, No. 237 (1988), pp. 213-215.

Ellinson, Vera M. et al., "New Antimicrobial Materials Based on Polymers With Nanostructured Surface Modified by Organic Fullerene [60] Derivatives," Plasma Processes and Polymers, vol. 6 (2009) pp. 585-591.

Ensing, G. T. et al., "Differences in Structure Between Antibiotic-Loaded Bone Cements (Palacos R-Ga nd Copal) and Beads (Septopal) Prior to and After Antibiotic Release," Structure of Antibiotic-Loaded Bone Cements and Beads, date unknown, 13 pages.

Eriksson, Ejnar "Achilles Tendon Surgery and Wound Healing," Knee Surg. Sports Traumatol, Arthrosc., 9:193, Editorial, Published online; May 23, 2001, 1 page.

Evans, Richard P. et al., "Gentamicin-Impregnated Polymethylmethacrylate Beads Compared with System Antibiotic Therapy in the Treatment of Chronic Osteomyelitis," Clinical Orthopaedics and Related Research, No. 295 (1993), pp. 37-42.

Faber, Christopher "Histatin and Lactoferrin-derived Antimicrobial Peptides; in Vitro and in Vivo Studies on the Treatment and Prevention of Osteomyelitis," Chapters 1-8 and Apendices, 2007 (133 pages).

Faber, Christopher et al., "In vivo Comparison of Dhvar-5 and Gentamicin in an MRSA Osteomyelitis Prevention Model," Journal of Antimicrobial Chemotherapy (2006), pp. 1-14.

Farnsworth, Kelly D. et al., "The Effect of Implanting Gentamicin-Impregnated Polymethylmethacrylate Beads in the Tarsocrural Joint of the Horse," Veterinary Surgery, vol. 30 (2001), pp. 126-131.

Fernandez-Fairen, M.D., Mariano et al., "Augmented Repair of Achilles Tendon Ruptures," The American Journal of Sports Medicine, vol. 25, No. 2 (1997), pp. 177-181.

"File History," for U.S. Appl. No. 11/774,495, Part 1 of 2, 309 pages.

"File History," for U.S. Appl. No. 11/774,495, Part 2 of 2, 326 pages.

"File History," for U.S. Appl. No. 13/242,837 297 pages.

"File History," for U.S. Appl. No. 12/349,312 263 pages.

Fish, D. N. et al., "Antibiotic-impregnated cement use in U.S. hospitals," Am J Hosp Pharm. 49(10):2469-74, Abstract only (1992), 1 page.

Flick, Arthur B. et al., "Noncommerical Fabrication of Antibiotic-impregnated Polymethylmethacrylate Beads," Clinical Orthopaedics and Related Research, No. 223 (1987), pp. 282-286.

Gitelis, Steven et al., "The Treatment of Chronic Osteomyelitis with a Biodegradable Antibiotic-Impregnated Implant," Journal of Orthopaedic Surgery 2002, 10(1), pp. 53-60.

Gonzalez, Della Valle A. et al., "Effective Bactericidal Activity of Tobramycin and Vancomycin Eluted from Acrylic Bone Cement," Acta Orthop Scand, 72 (3), 2001, pp. 237-40, abstract only (1 page).

Goodell, John A. et al., "Preparation and Release Characteristics of Tobramycin-impregnated Polymethylmethacrylate beads," American Journal of Hospital Pharmacy, vol. 43, 1986 (10 pages).

Gosselin, R. A. et al., "Antibiotics for Preventing Infection in Open Limb Fractures (Cochrane Review)," The Cochrane Library, Issue 3, 2006, abstract only (10 pages).

Greene, Thomas L. et al., "Soft Tissue Coverage for Lower-Extremity Trauma: Current Practice and Techniques," Journal of Orthopaedic Trauma, vol. 2, No. 2 (1988), pp. 158-173.

Gruninger, M.D., Robert P. et al., "Chapter 8: Antibiotic-Impregnated PMMA Beads in Bone and Prosthetic Joint Infections," Orthopaedic Infections,1989 (pp. 66-74).

Gunderson, Brent W. et al., "Synergistic Activity of Colistin and Ceftazidime against Multiantibiotic-Resistant Pseudomonas aeruginosa in an In Vitro Pharmacodynamic Model," Antimicrobial Agents and Chemotherapy, vol. 47, No. 3, 2003, (pp. 905-909).

Hain, M.D., Timothy C. "Gentamicin Ototoxicity," http://www.dizziness-and-balance.com/disorders/bilat/gentamicin%20toxicity.htm, downloaded 2006 (9 pages).

Hanssen, M.D., Arlen D. "Prophylactic Use of Antibiotic Bone Cement," The Journal of Arthroplasty, vol. 19, No. 4, Suppl. 1, 2004 (pp. 73-77).

(56) References Cited

OTHER PUBLICATIONS

Hanssen, MD, Arlen D. "Local Antibiotic Delivery Vehicles in the Treatment of Musculoskeletal Infection," Clinical Orthopaedics and Related Research, No. 437, 2005 (pp. 91-96).
Hanssen, MD, Arlen D. et al., "Local Antibiotic Delivery Systems, Where Are We and Where Are We Going?," Clinical Orthopaedics and Related Research, No. 437, 2005 (pp. 111-114).
Hanssen, MD, Arlen D. et al., "Treatment of the Infected Hip Replacement," Clinic Orthop, No. 420, 2004 (pp. 63-71).
Hardy, Mark A. "Current Controversies in Podiatry, Antibiotic Therapy in Open Fractures," http://www.podiatryonline.com/patient_care/how_to/antibiotic.cfm., downloaded 2006 (4 pages).
Henry, Stephen L. et al., "Antibiotic-Impregnated Beads," Orthopaedic Review, vol. XX, No. 3, 1991 (pp. 242-247).
Henry, Stephen L. et al., "Local Antibacterial Therapy for the Management of Orthopeadic Infections," Clinical Pharmacokinetics, 29(1), 1995 (12 pages).
Henry, Stephen L. et al., "Long-Term Implantation of Gentamicin-Polymethylmethacrylate Antibiotic Beads," Clinical Orthopaedics and Related Research, No. 295, 1993 (pp. 47-53).
Henry, Stephen L. et al., "The Antibiotic Bead Pouch Technique," Clinical Orthopaedics and Related Research, No. 295, 1993 (10 pages).
Henry, Stephen L. et al., "The Prophylactic Use of Antibiotic Impregnated Beads in Open Fractures," The Journal of Trauma, vol. 30, No. 10, 1990 (10 pages).
Hettiaratchy, Shehan et al., "Pathophysiology and Types of Burns," http://bmj.com/cgi/content/full/329/7458/148-b, downloaded 2007 (5 pages).
Hofmann, A. A. et al., "Treatment of Infected Total Knee Arthroplasty Using an Articulating Spacer," Clin Orthop Relat Res, 1995, 321:45-54, abstract only (1 page).
Hong, M.D., Joon P. et al., "The Use of Anterolateral Thigh Perforator Flaps in Chronic Osteomyelitis of the Lower Extremity," Plastic & Reconstructive Surgery, 2005,115(1):142-147, abstract only (1 page).
Hota, Md, Bala et al., "Corn munity-Associated Methicillin-Resistant *Staphylococcus aureus* Skin and Soft Tissue Infections at a Public Hospital," Arch Intern Med, vol. 167, 2007 (pp. 1026-1033).
"International Preliminary Report on Patentability," for PCT/US2013/065297, dated Apr. 30, 2015 (9 pages).
"International Search Report and Written Opinion," for PCT/US2007/072983, dated Dec. 8, 2008 (18 pages).
"International Search Report and Written Opinion," for PCT/US2013/065297, dated Jan. 3, 2014 (12 pages).
Jennings, A. G. et al., "Chronic Rupture of Tendo Achillis," The Journal of Bone and Joint Surgery, vol. 84-B, No. 3, 2002 (pp. 361-363).
Jiranek, William A. et al, "Antibiotic-Loaded Bone Cement for Infection Prophylaxis in Total Joint Replacement", J. Bone Joint Surg. Am, vol. 88, 2006, (15 pages).
Kakiuchi, Masaaki "A Combined Open and Percutaneous Technique for Repair of Tendo Achillis," The Journal of Bone and Joint Surgery, vol. 77-B, No. 1, 1995 (pp. 60-63).
Keating, J. F. et al., "Reamed nailing of open tibial fractures: does the antibiotic bead pouch reduce teh deep infection rate?," J Orthop Trauma, 10(5): 298-303, Abstract from www.pubmed.gov (1996), 1 page.
Klemm, K. "The Use of Antibiotic-Containing Bead Chains in the Treatment of Chronic Bone Infections," Clinical Microbiology and Infection, vol. 7, No. 1 (2001), pp. 28-31.
Klemm, Klaus W. "Antibiotic Bead Chains," Clinical Orthopaedics and Related Research, No. 295 (1993) pp. 63-76.
Krasko, Michal Y. et al., "Gentamicin Extended Release from an Injectable Polymeric Implant," Journal of Controlled Release, 117, 2007 (pp. 90-96).
Kwan, Ng W. et al., "Melioidotic Osteomyelitis Treated with Antibiotic-calcium Hydroxyapatite Composite: Case Report with Four-year Follow-up," Signapore Med J, 47(1), 2006 (pp. 71-74).

Lalliss, Maj Steven J. et al., "Optimization of Wound Irrigation," US Army Institute of Surgical Research, Ft. Sam Houston, TX (29 pages).
Leone, Md, James M. et al., "Management of Infection at the Site of a Total Knee Arthroplasty," The Journal of Bone & Joint Surgery, vol. 87-A, No. 10, 2005 (pp. 2336-2348).
Lindholm, Ake "A New Method of Operation in Subcutaneous Rupture of the Achilles Tendon," Acta chir. scandinav., vol. 117, 1959 (pp. 261-270).
Lyons, M.D., Val O. et al., "Bacterial Adherence to Plain and Tobramycin-Laden Polymethylmethacrylate Beads," Clinical Orthopaedics and Related Research, No. 278, 1992 (pp. 260-264).
Mader, Jon T. et al., "In Vitro Evaluation of Antibiotic Diffusion from Antibiotic-Impregnated Biodegradable," Antimicrobial Agents and Chemotherapy, vol. 41, No. 2, 1997 (2 pages).
Maffulli, Nicola et al., "Early Weightbearing and Ankle Mobilization after Open Repair of Acute Midsubstance Tears of the Achilles Tendon," The American Journal of Sports Medicine, vol. 31, No. 5, 2003 (paged 692-700).
Marculescu, Md, C. E. et al., "Prosthetic Joint Infection Diagnosed Postoperatively by Intraoperative Culture," Clinical Orthopaedics and Related Research, No. 439, 2005 (pp. 38-42).
Matsuno, H et al., "Anbiotic-Containing Hyaluronic Acid Gel as an Antibacterial Carrier: Usefulness of Spone and Film-formed HA Gel in Deep Infection," Uj. Orthop Res., 24(3), 2006 abstract only (2 pages).
McHale, Kathleen A. et al., "Treatment of Infected Tibial Nonunions with Debridement, Antibiotic Beads, and the Ilizarov Method," Military Medicine, vol. 169, 2004 (pp. 728-734).
Mclaren, Md, A. C. et al., "Phenolphthalein Used to Assess Permeability of Antibiotic Laden PMMA—A Pilot Study," Mulsculo Skeletal Infection Society, 2004 Abstract: BS 5, downloaded 2006 from http://www.msis-na.org/id83_m.htm, abstract only (2 pages).
McNamara, Md, David R. et al., "Advances in Therpaeutics and Diagnostics, Vancomycin," J. Am. Acad. Orthop. Surg, vol. 13, No. 2, 2005 (pp. 89-92).
Miclan, T. et al., "Bone Toxicity of Locally Applied Aminoglycosides," J. Orthop. Trauma, 9(5), 1995, abstract only (2 pages).
Moehring, M.D., H. D. et al., "Comparison of Antibiotic Beads and Intravenous Antibiotics in Open Fractures," Clinical Orthopaedics and Related Research, No. 372, 2000 (9 pages).
Mohanty, S. P. et al., "Use of Antibiotic-Loaded Polymethyl Methacrylate Beads in the Management of Musculoskeletal Sepsis—a Retrospective Study," Journal of Orthopaedic Surgery, vol. 11, No. 1, Jun. 2003 (pp. 73-79).
Movin, Tomas et al., "Acute Rupture of the Achilles Tendon," Foot Ankle Clin N Am, vol. 10, No. 2, Jun. 2005 (pp. 331-356).
Naraharisetti, Pavan K. et al., "In Vitro and In Vivo Release of Gentamicin from Biodegradable Discs," J Biomed Mater Res Part B: Appl Biomater 77B, 2006 (pp. 329-337).
Nelson, Carl J. et al., "A Comparison of Gentamicin-Impregnated Polymethylmethacrylate Bead Implantation to Conventional Parenteral Antibiotic Therapy in Infected Total Hip and Knee Arthroplasty," Clnical Orthopaedics and Related Research, No. 295, Oct. 1993 (pp. 96-101).
Nelson, Carl L. et al., "In Vitro Elution Characteristics of Commercially and Noncommercially Prepared Antibiotic PMMA Beads," Clinical Orthopaedics and Related Research, No. 284, Nov. 1992 (pp. 303-309).
Neut, Danielle et al., "Biomaterial-associated infection of gentamicin-loaded PMMA beads in orthopaedic revision surgery," Journal of Antimicrobial Chemotherapy, No. 47, 2001 (10 pages).
Nix, David E. et al., "Antibiotic Tissue Penetration and Its Relevance: Impact of Tissue Penetration on Infection Response," Antimicrobial Agents and Chemotherapy, vol. 35, No. 10m 1991 (8 pages).
"Non-Final Office Action," for U.S. Appl. No. 14/055,654, dated Jan. 16, 2015 (9 pages).
"Notice of Allowance," for U.S. Appl. No. 14/055,654, dated Jun. 9, 2015 (36 pages).
Ostermann, Peter A. et al., "The Role of Local Antibiotic Therapy in the Management of Compound Fractures," Clinical Orthopaedics and Related Research, No. 295, Oct. 1993 (pp. 102-111).

(56) References Cited

OTHER PUBLICATIONS

Ostermann, Peter A. et al., "Timing of Wound Closure in Severe Compound Fractures," Orthopedics, vol. 17, No. 5, May 1994 (5 pages).
Ostermann, Peter et al., "Local Antibiotic Therapy for Severe Open Fractures," The Journal of Bone and Joint Surgery, vol. 77-B, Jan. 1995 (pp. 93-97).
Owen, M R. et al., "Management of MRSA Septic B Arthritis in a Dog Using a Gentamicin Impregnated Collagen Sponge," Journal of Small Animal Practice, (2004), 45, http://tahilla. typepad.com/petsmrsa/2004/12/management_ of_m.html, downloaded May 1, 2006 (11 pages).
Patel, M.D., Robin et al., "The Diagnosis of Prosthetic Joint Infection," Clinical Orthopaedics and Related Research, No. 437, Aug. 2005 (pp. 55-58).
Patzakis, Michael J. et al., "Prospective, Randomized, Double-Blind Study Comparing Single-Agent Antibiotic Therapy, Ciprofloxacin to Combination Antibiotic Therapy in Open Fracture Wounds," Journal of Orthopaedic Trauma, vol. 14, No. 8, 2000 (6 pages).
Perry, M.D., Archie C. et al., "Antimicrobial Release Kinetics from Polymethylmethacrylate in a Novel Continuous Flow Chamber," Clinical Orthopaedics and Related Research. 2002, 3 pages.
Phadke, S. M. et al., "Lentivirus Jytec Peptide 1 Perturbs Outer and Inner Membrane of Serratia Marcescens," J. Antimicrobial Agents & Chemotherapy, 46(6), 2002 (pp. 2041-2045).
Phadke, S. M. et al., "Selective Toxicity of Engineered Lentivirus Lytic Peptides in a CF Airway Cell Model," Peptides, vol. 24, 2003 (pp. 1099-1107).
Pollak, Andrew N. et al., "Extremity War Injuries: State of the Art and Future Directions, Prioritized Future Research Objectives," Journal of the American Academy of Orthopaedic Surgeons, vol. 14, No. 10, 2006 (pp. S212-S214).
Polly, Jr., David W. et al., "Advanced Medical Care for Soldiers Injured in Iraq and Afghanistan," MMA Publication, Minnesota Medicine, vol. 87, Nov. 2004 (pp. 1-6).
Popham, G. J. et al., "Antibiotic-Impregnated Beads," Orthopaedic Review, vol. XX, No. 4, Apr. 1991 (pp. 331-337).
"Response to Non-Final Office Action," for U.S. Appl. No. 14/055,654, dated Jan. 16, 2015 and filed May 18, 2015 (7 pages).
Roeder, Brett et al., "Antibiotic Beads in the Treatment of Diabetic Pedal Osteomyelitis," The Journal of Foot & Ankle Surgery, vol. 39, No. 2, Mar./Apr. 2000 (pp. 124-129).
Rotschafer, Pharmd, John et al., "In Vitro Characterization of Tobramycin Coated Beads Combined with Tobramycin-Sensitive and -Resistant Strains of Acinetobacter baumannii, Pseudomonas aeruginosa, *Staphylococcus aureus* and *Staphylococcus epidermidis*," May 2007 (pp. 1-27).
Sayegh, Ayman I. et al., "Polymethylmethacrylate Beads for Treating Orthopedic Infections," Copendiium, vol. 25(10), 2003 (pp. 788-795).
Schmidt, Andrew H. et al., "Pathophysiology of Infections after Internal Fixation of Fractures," J Am Acad Orthop Surg, 2000, vol. 8, No. 5, Sep./Oct. 2000, pp. 285-291.
Scott, C P. "Effectiveness of bone cement containing tobramycin: an in vitro susceptibility study of 99 organisms found in infected joint arthoplasty," Journal of Bone and Joint Surgery, http://findarticles.com/p/articles/mi_qa3767/is_199905/ai_n8845754/print, Aug. 8, 2007 (6 pages).
Scott, David M. et al., "Use of Vancomycin and Trobramycin Polymethylmethacrylate Impregnated Beads in the Management of Chronic Osteomyelitis," Drug Intelligence and Clinical Pharmacy, vol. 22, Jun. 1988 (pp. 480-483).
Seeley, Stacy K. et al., "vol. And Surface Area Study of Tobramycin-Polymethylmethacrylate Beads," Clin. Orthop., No. 420, Mar. 2004 (pp. 298-303).
Seligson, D. et al., "Antibiotic-leaching from polymethylmethacrylate beads," The Journal of Bone & Joint Surgery, vol. 75, 1993 (8 pages).

Seligson, David et al., "The Management of Open Fractures Associated with Arterial Injury Requiring Vascular Repair," The Journal of Trauma, vol. 37, No. 6, Dec. 1994 (5 pages).
Seligson, David et al., "The Use of Antibiotic-Impregnated Polymethylmethacrylate Beads to Prevent the Evolution of Localized Infection," Journal of Orthopaedic Trauma, vol. 6, No. 4, 1992 (pp. 401-406).
"Septopal," Biomet Europe, http://www.biometeurope.com/index.php?id=232, Oct. 30, 2007, 5 pages.
Sirkin, M et al., "A staged protocol for soft tissue management in the treatment of complex pilon fractures," J. Orthop Trauma, 15(8); http://www.ncbi.nlm.nih.gov/sites/entrez?cmd-Retrieve&db=PubMed&list_uids=10052780, downloaded Jul. 9, 2007 (2 pages).
Smith & Nephew, "Wound Bed Preparation," http://wound.smith-nephew.com/us/popup.asp?NodeId-2630&Hide-True&Tab=, downloaded May 1, 2006 (2 pages).
Stevens, C M. et al., "An Articulated Antibiotic Spacer Used for Infected Total Knee Arthroplasty: A Comparitive in Vitro Elution Study of Simplex and Palacos Bone Cements," J. Orthop. Res., Jan. 2005; 23(1):27-33; 1 page from http://www.ncbi.nim.nih.gov/entrez/query.fcgi?itool=abstractplus&db=bupmed&cmd, downloaded Aug. 9, 2006.
"STIC Search Results," for chemical name and molecular information for tetrakis (4-benzophenylmethoxymethyl)methane (1 page).
Stone, Patrick A. et al., "Use of Antibiotic-Loaded Polymethylmethacrylate Beads for the Treatment of Extracavitary Prosthetic Vascular Graft Infections," Journal of Vascular Surgery, vol. 44, No. 4, Oct. 2006 (pp. 757-761).
Suzuki, A et al., "A biodegradable delivery system for antibiotics and recombinant human bone morphogenetic protein-2: A potential treatment for infected bone defects," J. Orthop. Res., Mar. 2006; 24(3): 327-32, p. 1 from http://www.ncbi.nlm.nih.gov/sites/entrez?cmd-Retrieve&db=PubMed&list_uids-16479565., downloaded Jul. 9, 2007.
Templeman, David "Advances in the Treatment of Tibial Shaft Fractures: A Current Concepts Review," from http://www.medscape.com:/viewprogram/248_pnt, downloaded Aug. 8, 2007 (pp. 1-15).
Tencza, S. B. et al., "Lentivirus-Derived Antimicrobial Peptides: Increased Potency by Sequence Engineering and Dimerizaion," J. Antimicrobial Agents & Chemotherapy, 44(1), 1999 (pp. 33-41).
Tencza, S. B. et al., "Novel Antimicrobial Peptides Derived From Human Immunodeficiency Virus Type 1 and Other Lentivirus Transmembrane Proteins," J. Antimicrobial Agents & Chemotherapy, 41(11), 1997 (pp. 2394-2398).
Tornetta, Paul I. et al., "The Use of Solid Form-Fitting Antibiotic Cement Spacers in Bone Loss of the Tibia," OTA 2004 Posters, Jul. 25, 2006 (pp. 1-2).
U.S. Dept. of Health & Human Services, "CLASS II Special Controls Guidance Document: Polymethylmethacrylate (PMMA) Bone Cement; Guidance for Industry and FDA," Food and Drug Administration, Center for Devices and Radiological Health, Jul. 17, 2002, pp. 1-18.
Von Frauhofer, J. A. et al., "Leaching of tobramycin from PMMA bone cement beads," Journal of Biomedical Materials Research, vol. 19, 1985 (pp. 751-756).
Wahlig, H. et al., "The Release of Gentamicin from Polymethylmethacrylate Beads," The Journal of Bone and Joint Surgery, vol. 60-B, No. 2 (1978) pp. 270-275.
Walenkamp, Geert et al., "Gentamicin Pmma Beads, Pharmacokinetic and Nephrotoxicological Study," Clinical Orthopaedics and Related Research, No. 205, 1986 (7 pages).
Wang, Gahin et al., "The Release of Cefazolin and Gentamicin from Biodegradable PLA/PGA Beads," International Journal of Pharmaceutics, 273, 2004 (pp. 203-212).
Weitz-Marshall, Amanda D. et al., "Timing of Closure of Open Fractures," Journal of the American Academy of Orthopaedic Surgeons, vol. 10, No. 6 Nov./Dec. 2002, 379-383.
Wenke, J.C. et al., "Effectiveness of Commercially-Available Antibiotic-Impregnated Implants," The Journal of Bone & Joint Surgery (Br), vol. 88-B, No. 8 Aug. 2006, 1102-1104.
Wheeless' Textbook of Orthopaedics, "Addition of Antibiotics to Cement" from http://www.wheelessonline.com/ortho/comparison_of_antibiotics_to_cement, downloaded May 10, 2006, 1-3.

(56) References Cited

OTHER PUBLICATIONS

Wheeless' Textbook of Orthopaedics, "Comparison of the Clinical Efficacy and Tolerance of Gentamicin Beads," from http://www.wheelessonline.com/ortho/comparison_of_the_clinical_efficacy_and_ tolerance, downloaded May 10, 2006 (1 page).

Wilson, Katharine J. et al., "Comparative Evaluation of the Diffusion of Tobramycin and Cefotaxime Out of Antibiotic-Impregnated Polymethylmethacrylate Beads," Journal of Orthopaedic Research, vol. 6, No. 2 1988, (pp. 278-286).

Wininger, David A. et al., "Antibiotic-Impregnated Cement and Beads for Orthopedic Infections," Antimicrobial Agents and Chemotherapy, vol. 40, No. 12 Dec. 1996, 2675-2679.

Wu, Peng et al., "Drug/Device Combinations for Local Drug Therapies and Infection Prophylaxis," Biomaterials 27 2006, 2450-2467.

Wu, Peng et al., "Orthopedic Device-Based Drug Delivery," Article in Press, Biomaterials, date unknown (3 pages).

Young, Jonathan S. et al., "Achilles Tendon Rupture and Tendinopathy: Management of Complications," Foot Ankle Clin N Am., vol. 10, No. 2 2005, 371-382.

Yung, Anthony C. et al., "Diabetes Watch: Can Antibiotic Beads Have an Impact in Osteomyelitis Cases?," Podiatry Today Oct. 2003, Issue 10: (6 pages).

Zalavras, Charalampos et al., "Local Antibiotic Therapy in the Treatment of Open Fractures and Osteomyelitis," Clinical Orthopaedics and Related Research, No. 427 Oct. 2004, 86-93.

Zalavras, Charalampos et al., "Open Fractures: Evaluation and Management," Journal of the American Academy of Orthopaedic Surgeons, vol. 11, No. 3, May/Jun. 2003, 212-219.

Zellweger, G. et al., "Infection in the Upper Body: Hand and Burn-Wound Microbiology and Considerations for Antimicrobial Therapy," Journal of Burn Care & Rehabilitation, vol. 13, No. 2, Part 2 Mar./Apr. 1992, 298-304.

Decoster, T. A. "Management of Traumatic Foot Wounds," Journal of the American Academy of Orthopedic Surgeons, vol. 2, No. 4, Jul./Aug. 1994, pp. 226-230.

"International Search Report and Written Opinion," for PCT/US2015/043181 dated Nov. 25, 2015 (11 pages).

"Response to Communication Pursuant to Rules 161 (1) and 162 EPC," for European Patent Application No. 13783782.9, dated Jun. 18, 2015 and filed with the EPO Dec. 23, 2015 (14 pages).

Seligson, D. "Leaching of Tobramycin from PMMA Bone Cement Beads," Journal of Biomaterials Research, vol. 19, 1985, pp. 751-756.

"Communication Pursuant to Article 94(3) EPC," for European Patent Application No. 13783782.9 dated Dec. 23, 2016 (4 pages).

"International Preliminary Report on Patentability," for PCT Application No. PCT/US2015/043181 dated Feb. 17, 2017 (8 pages).

"Non-Final Office Action," for U.S. Appl. No. 14/819,955 dated Feb. 8, 2018 (51 pages).

"Response to Non-Final Office Action," for U.S. Appl. No. 14/819,955, dated Feb. 8, 2018 and filed Mar. 27, 2018 (9 pages).

"Communication Pursuant to Article 94(3) EPC," for European Patent Application No. 15759568.7 dated Jun. 4, 2018 (5 pages).

Loo, Ching-Lee et al., "Superhydrophobic, nanotextured polyvinyl chloride films for delaying Pseudomonas aeruginosa attachment to intubation tubes and medical plastics," Acta Biomater. May 2012;8(5):1881-90 (10 pages).

\* cited by examiner

WOUND PACKING DEVICE WITH NANOTEXTURED SURFACE

This application claims the benefit of U.S. Provisional Application No. 62/032,244 filed Aug. 1, 2014, the contents of which are herein incorporated by reference.

FIELD OF THE INVENTION

The present invention relates to wound packing devices. More specifically, the present invention relates to wound packing devices with nanotextured surfaces and methods of making and using the same.

BACKGROUND OF THE INVENTION

Wound care is critical to ensure optimal healing of wounds and prevent infection. Wound healing includes sequential phases of inflammation, proliferation, and remodeling. Specific types of wounds require special care in order to reach optimal results. By way of example, in the context of deep wounds, abscesses and/or infections can occur deep in the wound bed if the outermost portion of the wound heals over too quickly.

Materials used to treat wounds include creams, foams, gels, ointments, pads, pastes, powders, or other materials. Some of these may include an antimicrobial that can be released into the wound bed.

SUMMARY OF THE INVENTION

Embodiments of the invention include wound packing devices with nanotextured surfaces and methods of making and using the same. In an embodiment, the invention includes a wound packing device including a plurality of spacing elements having a nanotextured surface. The surface of the spacing elements can resist colonization by microorganisms. The wound packing device can also include a connector connecting the plurality of spacing elements to one another.

In an embodiment, the invention includes a wound packing device including a plurality of spacing elements, the spacing elements including a nanotextured surface. The wound packing device can also include a container, the plurality of spacing elements disposed within the container.

In an embodiment, the invention includes a method of making a wound packing device. The method can include forming a plurality of spacing elements, the spacing elements including a nanotextured surface. The method can further include mounting the plurality of spacing elements on a connector.

In an embodiment, the invention can include a wound packing kit. The kit can include a plurality of spacing elements, the spacing elements including a nanotextured surface. The spacing elements can include a surface that resists colonization by microorganisms. The kit can further include a connector connecting the plurality of spacing elements to one another; the connector comprising a fitting to allow for the number of spacing elements connected to one another by the connector to be modified by an end user.

In an embodiment, the invention can include a method of treating wounds. The method can include dispensing a wound packing device from a sterile package. The wound packing device can include a plurality of spacing elements, the spacing elements including a nanotextured surface, the plurality of spacing elements configured to absorb exudate, and a connector connecting the plurality of spacing elements to one another. The method can further include inserting the wound packing device into a wound bed.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

Figures 1, 2:
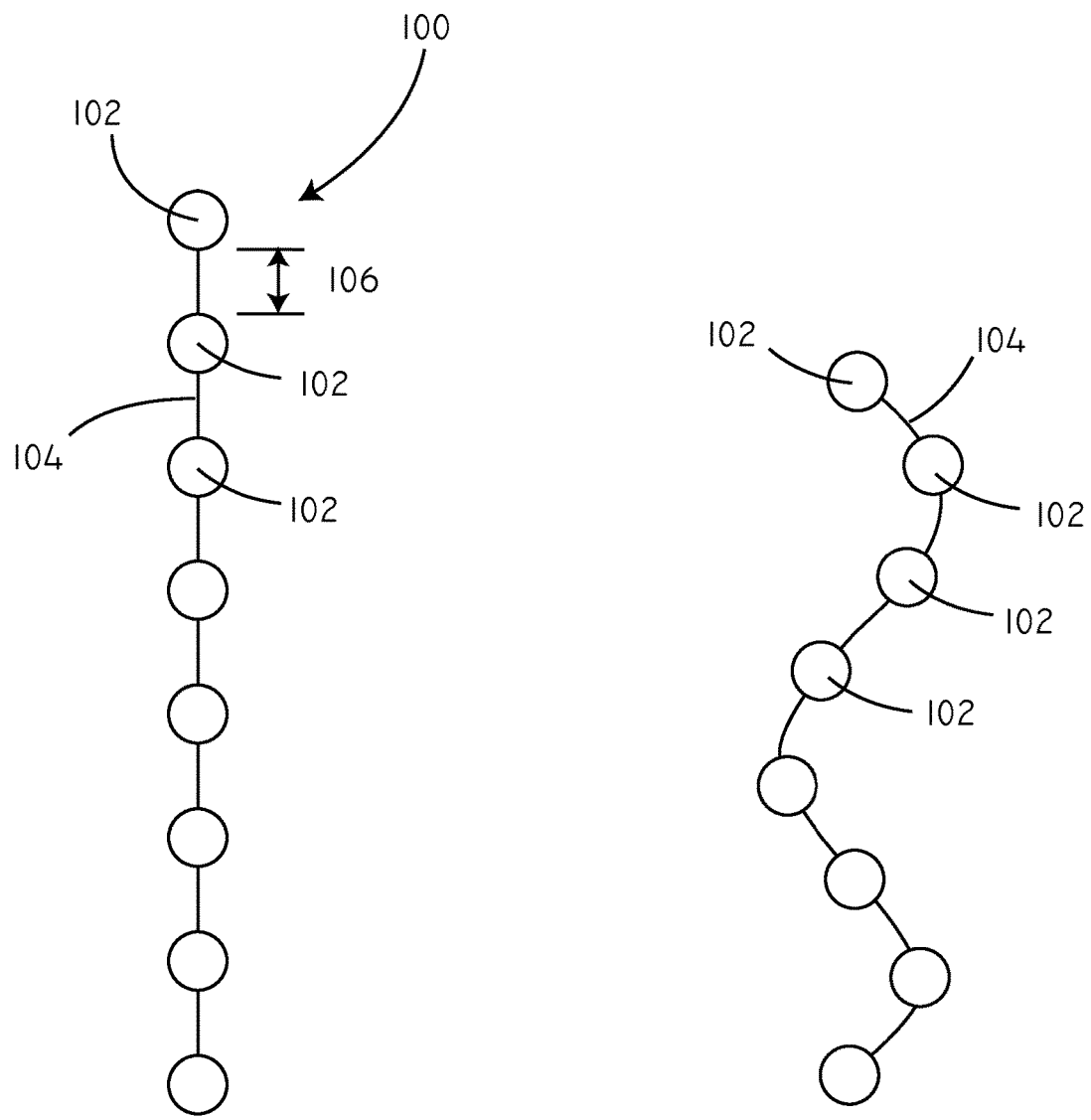
FIG. 1 is a schematic view of a wound packing device in accordance with various embodiments of the invention.
FIG. 2 is a schematic view of a wound packing device in accordance with various embodiments of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Embodiments of the invention include wound packing devices that are effective for wound care management. In particular embodiments herein include a wound packing device including a nanotextured surface is included. As used herein, the term "nanotextured" refers to surface characteristics on a nanometer scale. Surface characteristics can include surface topology or roughness, surface charge and/or hydrophobicity. In various embodiments surfaces herein can be characterized by one or more of surface roughness, surface charge, and/or hydrophobicity that can decrease, inhibit, and/or reduce the ability of microorganisms, and in particular bacteria, to adhere to, proliferate on, and/or colonize the surface.

Some embodiments of the invention include beaded wound spacer devices having multiple beads connected by a non-absorbable suture material. The beads and/or suture material can have surface nanotexturing characteristics to provide advantages as described herein. Exemplary beaded wound spacer devices include devices of various polymeric materials that are conducive to etching or scoring to produce a nanotextured surface. Without being limiting, examples of such beaded wound spacer devices are described in U.S. Pat. Nos. 8,685,421 and 8,697,106 (both to Kloke et al.), the entire content of which are hereby incorporated by reference herein.

The nanotextured surface can take the appearance of etching on the surface of the medical device, for example in the geometry or structural features of lines, points, hills, mounds, valleys, slopes and the like and distances between such geometries and structural features of various nanometer dimensions such as height and/or width and or length and/or depth having dimensions in the range from about 1 nanometer to about 1000 nanometers. For example nanoscale features within the scope herein include those having dimensions between about 10 nanometers to about 900 nanometers, about 100 nanometers to about 500 nanometers, about 1 nanometer to about 100 nanometers, about 10 nanometers to about 50 nanometers, about 1 nanometer to about 10 nanometers, about 1 nanometer to about 5 nanometers, about 10 nanometers to about 100 nanometers, and any ranges in between the above ranges. In some embodiments the lines of etching are spaced about 600 nm from each other. In other embodiments the lines of etching are spaced about 500 nm from each other.

It will be appreciated that nanotextured surfaces can be formed in various ways. Aspects of nanotextured surface are described in U.S. Publ. Appl. No. 2013/0199539 (to Webster), the content of which is herein incorporated by reference in its entirety. In some embodiments, material can be removed from a surface to leave a nanotextured surface. In other embodiments, material can be deposited onto a surface to create a nanotextured surface. For example, the same or different from the material of the substrate surface can be deposited on the surface of the substrate using deposition methods including, but not limited to, sputtering, vapor deposition, spraying, and the like. In still other embodiments, a surface can be stamped, molded, pressed, or otherwise imprinted or contacted with a surface of another object to create a nanotextured surface. Additionally the surface can be chemically etched or mechanically polished to achieve the desired nanotextured surface.

In yet other process embodiments antimicrobial activity can be imparted to surfaces of natural, biocompatible, biodegradable or synthetic polymeric materials (for example, but not limited to, chitosan, nylon and polyethylene terephthalate) by production of nanostructured surfaces. Exemplary processes include, but are not limited to, plasma treatment, or plasma treatment followed by treatment with organic fullerene [60] derivatives. The resulting nanostructured surfaces produced using these processes exhibit increased antimicrobial activity when compared with "untreated" control surfaces (Plasma Process. Polym.; *New Antimicrobial Materials Based on Polymers with Nano-structured Surface Modified by Organic Fullerene [60] Derivatives*; Ellinson et al., 2009, 6, S85-S91).

In various embodiments, a portion of the substrate surface can be removed by action of a nano-roughing agent. Mechanisms for removing material from a substrate surface include abraiding, degrading, dissolution, etching and the like to produce a nanometer scale surface roughness. Particular methods include contacting the surface of the substrate with a device that will remove material from the substrate surface, such as by friction or abrasion. Alternatively, a liquid or gaseous material can be applied to the surface of the substrate to degrade, dissolve or etch away material from the surface of the substrate to produce a nanometer scale surface roughness. Such treatments are referred to as chemical treatments and include liquid or gaseous materials such as acids, bases, lipases, dichloroethylene and xylene and the like. Exemplary nano-roughing agents include one or more of an acid, a base, an alcohol, a peroxide, isoamyl acetate, dichloromethane, isoamyl acetate with zinc, dichloromethane with zinc, acetic acid, sulfuric acid, nitric acid, perchloric acid, phosphoric acid, hydrochloric acid, chloroform, acetone, ethanol, ammonia, sodium hydroxide, potassium hydroxide, ammonium hydroxide, ammonium fluoride, hydrofluoric acid, triflic acid, hydrogen peroxide, dichloroethylene, xylene, bacterial lipases, and the like.

In some embodiments, bacterial lipase solutions are used to produce a nanometer scale surface roughness on a substrate. According to this aspect, substrate surfaces are contacted with lipases, for example from *C. cilindracea* and *R. arrhisus*, in a manner to cause enzymatic degradation of the substrate and nanometer scale features on the surface of the substrate. In this manner, a method is provided to create a nanometer scale surface roughness having antibacterial properties by contacting the surface of a substrate with one or more lipases for a period of time to allow enzymatic degradation of surface materials thereby creating nanometer scale features on the surface of the substrate. In addition to lipases from *C. cilindracea* and *R. arrhisus*, other useful lipases include those from *Candida rugosa, Thermus thermophilus, Candida Antarctica, Aspergillus niger, Aspergillus oryzae, Aspergillus* sp, *Burkholderia* sp, *Candida utilis, Chromobacterium viscosum, Mucor javanicus, Penicillium roqueforti, Pseudomonas cepacia* and the like. Other useful lipases and etchants include phospholipases, sphingomyelinases, hepatic lipase, endothelial lipase, lipoprotein lipase, bile salt dependent lipase, pancreatic lipase, lysosomal lipase, hormone-sensitive lipase, gastric lipase, pancreatic lipase related protein 2, pancreatic lipase related protein 1, lingual lipase and the like.

Referring now to FIG. 1, a schematic view of a wound packing device 100 is shown in accordance with various embodiments of the invention. The wound packing device 100 includes a plurality of spacing elements 102 and a connector 104 connecting the plurality of spacing elements 102 to one another. In some embodiments, the wound packing device 100 can include from about 4 to 50 spacing elements 102. However, it will be appreciated that other numbers of spacing elements 102 can be included in other embodiments. The spacing elements 102 can be of various shapes and sizes. In some embodiments, the surface of the spacing elements 102 can be substantially smooth. In other embodiments, the surface of the spacing elements 102 can be textured. In some embodiments the surface of the spacing elements 102 can include grooves. The spacing elements 102 can be sized such that their major dimension is from about 0.5 mm to about 25 mm. For example, in some embodiments the major diameter of the spacing elements 102 can be from about 0.5 mm to about 2.5 mm. In some embodiments, the surface of the spacing elements 102 is deformable. In other embodiments, the surface of the spacing elements 102 is substantially rigid.

The distance 106 between adjacent spacing elements 102 along connector 104 in some embodiments can be at least equal to the largest dimension of the spacing elements 102. In some embodiments, the distance 106 between adjacent spacing elements along the connector is at least equal to the diameter of the spacing elements 102. In various embodiments, the distance 106 between adjacent spacing elements can be greater than 0.5 mm, 1.0 mm, 2.0 mm, 3.0 mm, 4.0 mm, 5.0 mm, 10 mm, 15 mm, 20 mm, or in some cases even greater than 25 mm. In yet other embodiments, distances 106 between spacing elements 102 can vary along the total length of the wound packing device 100. That is, the connectors 104 can be of various sizes along a single wound packing device 100. In some embodiments the connector has a diameter of about 0.1 mm to about 2 mm. In some embodiments the connector has a length of about 5 cm to about 200 cm.

The surface of the spacing elements and/or the connector can be configured to resist colonization by microorganisms. In some embodiments, the surface of the spacing elements and/or connector can have antimicrobial activity. In some embodiments, the surface of the spacing elements and/or connector can include silver ions or graphene. In some embodiments, the surface of the spacing elements and/or connector can include quaternary amines. In some embodiments, the surface of the spacing elements and/or connector can include tobramycin.

In certain embodiments, the surface of the spacing elements and/or connector can include aminoglycoside antibiotics, such as tobramycin, vancomycin, amikacin, gentamicin, kanamycin, neomycin, netilmicin, paromomycin, streptomycin, and apramycin. Other active agents on or in the surface of the spacing elements can include, for example, various modified aryls, and cationic steroidal antibiotics.

Additional suitable active agents on or in the surface include, for example, antimicrobial peptides such as those taught in U.S. Pat. No. 5,714,577 (Antimicrobial peptides); U.S. Pat. No. 5,945,507 (Antimicrobial peptides); U.S. Pat. No. 6,835,713 (Virus derived antimicrobial peptides); and U.S. Pat. No. 6,887,847 (Virus derived antimicrobial peptides), all of which are incorporated by reference in their entirety.

In some embodiments the spacing element comprises a polymer selected from the group consisting of polyamide, poly(methyl methacrylate), poly(ether blocked amides) (PEBAX), polyurethane, silicone, nylon, fluoropolymers and combinations thereof. In certain embodiments the spacing elements can be composed of a medical grade polymer.

The plurality of spacing elements 102 can be capable of absorbing exudate from a wound bed. In some embodiments, each spacing element 102 can be capable of absorbing an amount of exudate equal to at least the weight of the spacing element 102. In some embodiments, each spacing element 102 can be capable of absorbing an amount of exudate that is equal to a multiple of the weight of the spacing element 102. For example, in some embodiments each spacing element 102 can be capable of absorbing an amount of exudate that is equal to at least 2 times, 3 times, 4 times, or 5 times the weight of the spacing element 102.

In some embodiments, the plurality of connectors 104 can also be capable of absorbing exudate from a wound bed. In some embodiments, each connector 104 can be capable of absorbing an amount of exudate equal to at least the weight of the connector 104. In some embodiments, each connector 104 can be capable of absorbing an amount of exudate that is equal to a multiple of the weight of the connector 104. For example, in some embodiments each connector 104 can be capable of absorbing an amount of exudate that is equal to at least 2 times, 3 times, 4 times, or 5 times the weight of the connector 104.

The connector 104 can be flexible. For example, the connector 104 can bend freely in some embodiments so that the wound packing device 100 can assume a bunched or compacted configuration. The wound packing device 100 is sufficiently flexible to be bent into a U-shape. Referring now to FIG. 2, a schematic view of the wound packing device 100 is shown with the connector 104 bent in several places such that the wound packing device is curved and the spacing elements 102 are no longer in a straight line. In some embodiments the spacing elements 102 cannot be in the same plane due to the orientation of the bent connectors 104.

Figure 3:
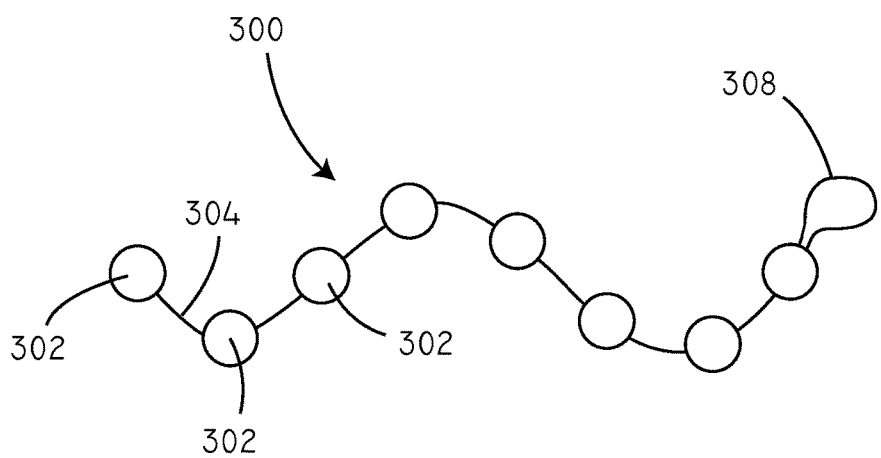
FIG. 3 is a schematic view of a wound packing device in accordance with various embodiments of the invention.

In some embodiments, the wound packing device can include a structural feature in order to secure the wound packing device to something else, secure an end of the wound packing device back onto itself or secure the wound packing device to another wound packing device. By way of example, an end of the wound packing device can include a loop of material that can be used to attach the wound packing device to something else, another wound packing device or back onto itself. Referring now to FIG. 3, a schematic view of a wound packing device 300 is shown in accordance with various embodiments of the invention. The wound packing device 300 includes a plurality of spacing elements 302 and a connector 304. The wound packing device 300 also includes a loop 308 of material which can be used to affix the end of the wounding packing device 300 to something else. By way of example, a user can pass a suture through the loop 308 in order to secure the wound packing device 300 to something else. For example, suture material can be passed through loop 308 to secure the wound packing device 300 for easy removal from a wound. Alternatively, the loop 308 can be passed over the other end of the wound packing device so that the two opposite ends of the wound packing device 300 are held adjacent to one another.

Figure 3A:
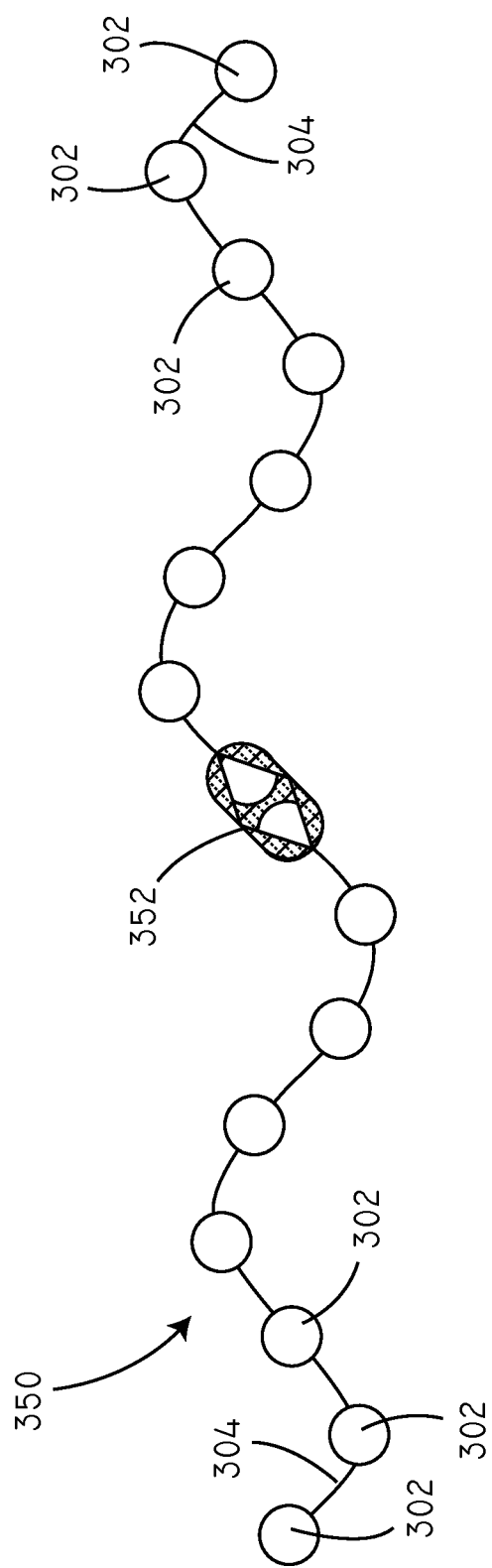
FIG. 3A is a schematic view of a wound packing device in accordance with various embodiments of the invention.

In yet other embodiments a first wound packing device can be attached to a second wound packing device to extend the length of the wound packing device. The attachment can be achieved using a spacing element coupling device. Referring now to FIG. 3A, a schematic view of a wound packing device 350 is shown in accordance with various embodiments of the invention. The wound packing device 350 includes spacing elements 302 and connectors 304. The wound packing device 350 includes a spacing element coupling device 352. By way of example, one end of the spacing element coupling device 352 can be appropriately sized to slip over connector 304 and retain the spacing element 302 on one end of a first wound packing device and the other unoccupied end of the spacing element coupling device 352 can slip over the spacing element 302 of a second wound packing device, resulting in an extended wound packing device 350. The spacing element coupling device 352 can be similar in function to metal light pull chain extenders used to extend light pull chains on household light pull switches.

Figure 4:
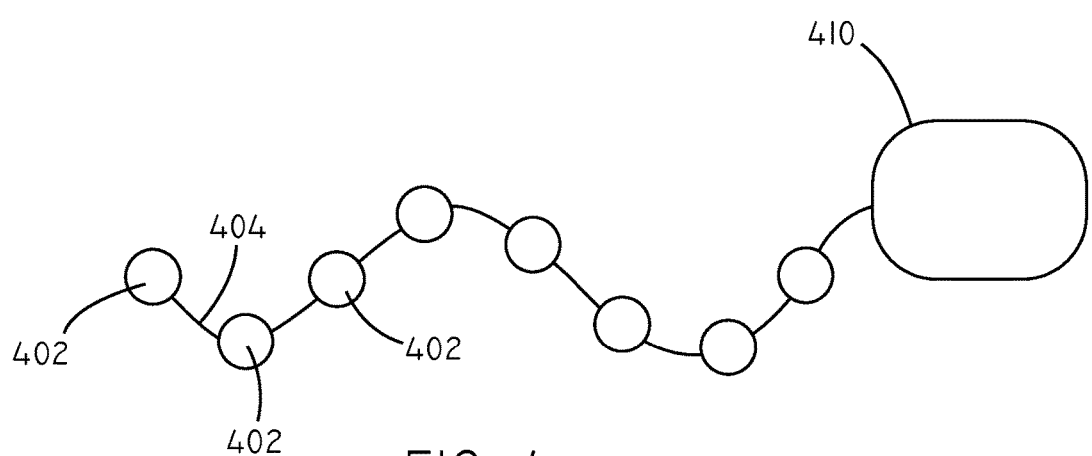
FIG. 4 is a schematic view of a wound packing device in accordance with various embodiments of the invention.

In some embodiments, the wound packing device can include a reservoir to retain wound exudate. In some embodiments, the reservoir is an external structure separate from other components of the wound packing device. In other embodiments, the reservoir is a structure disposed within the spacing elements or the connector. Referring now to FIG. 4, a schematic view of a wound packing device 400 is shown in accordance with various embodiments of the invention. The wound packing device 400 includes a plurality of spacing elements 402 and a connector 404. The wound packing device 400 also includes a reservoir 410. The reservoir 410 can define an interior volume that can retain exudate material. By way of example, in some embodiments the connector 404 can include a lumen or channel that can be in fluid communication with the reservoir 410, and exudate can pass through the connector 404 into the reservoir 410.

Figure 5:
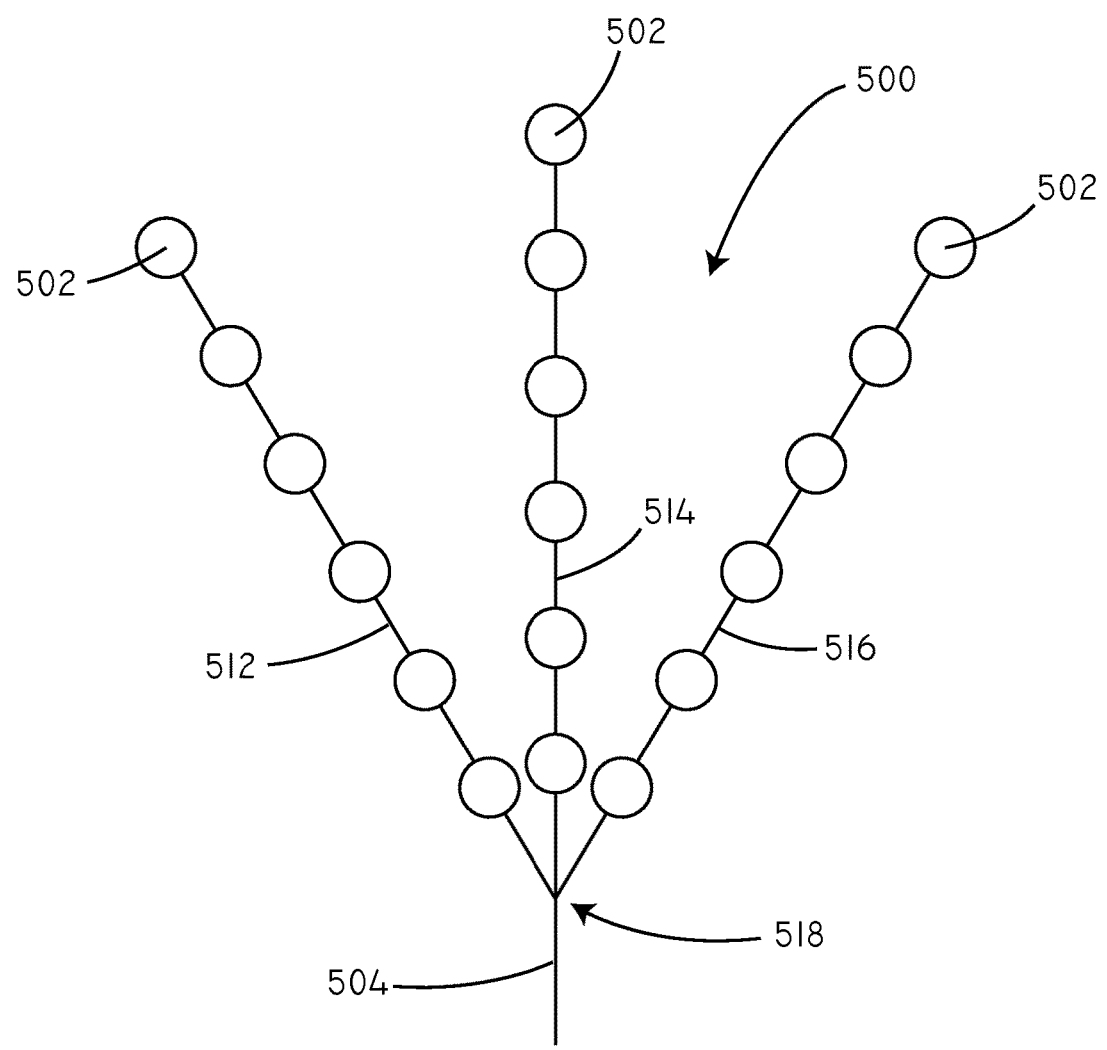
FIG. 5 is a schematic view of a wound packing device in accordance with various embodiments of the invention.

The spacing elements can be disposed along the connector in series with one another. In some embodiments, the spacing elements can be disposed along the connector such that one or more spacing elements are disposed in parallel with one or more other spacing elements. The connector can be one continuous piece or it can include multiple segments or branches. Referring now to FIG. 5, a schematic view of a wound packing device in accordance with various embodiments of the invention is shown. The wound packing device 500 can include a plurality of spacing elements 502 and connectors 504. The connector 504 can include a first branch 512, a second branch 514, and a third branch 516, that intersect one another at a point 518 on the connector 504.

Figure 6:
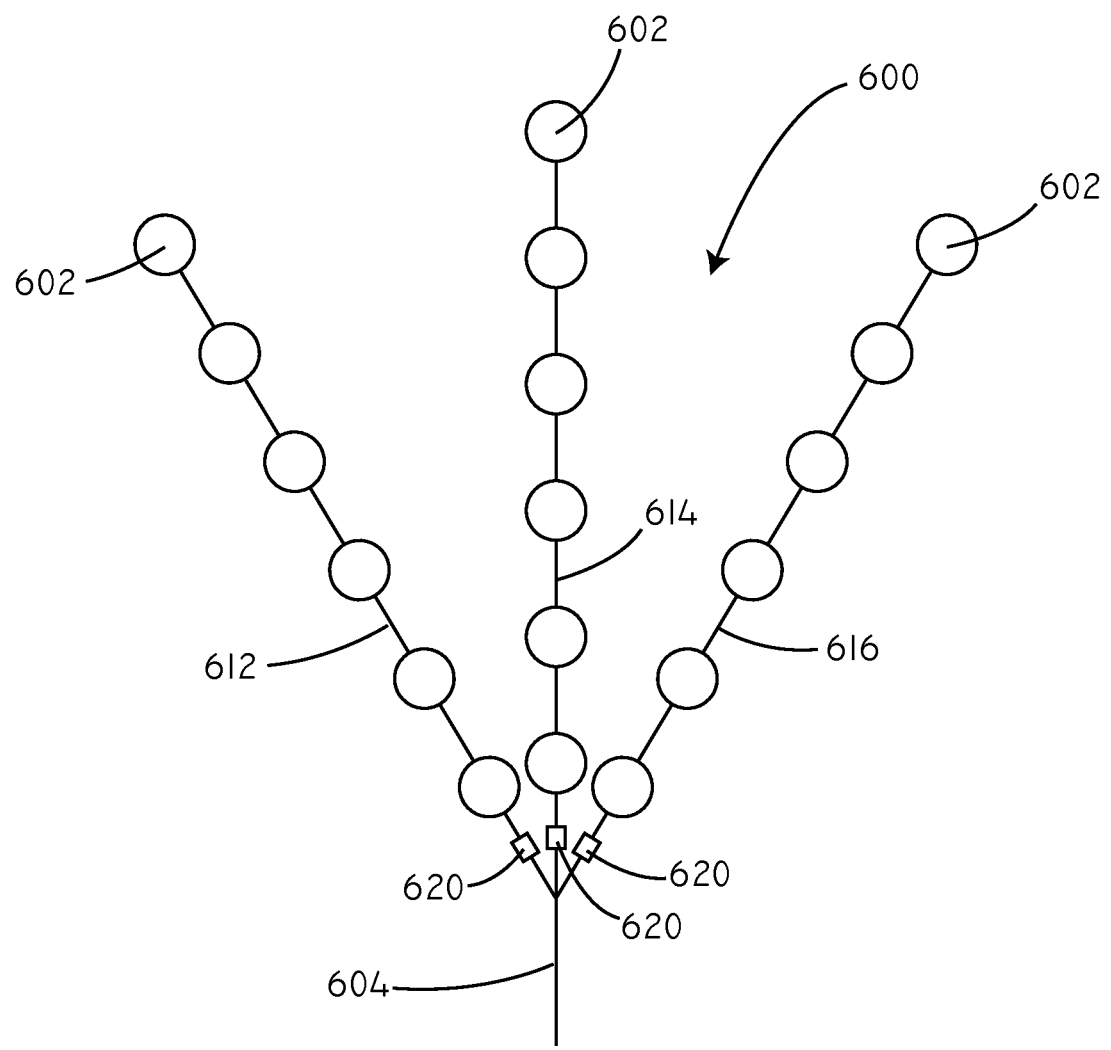
FIG. 6 is a schematic view of a wound packing device in accordance with various embodiments of the invention.
Figure 7:
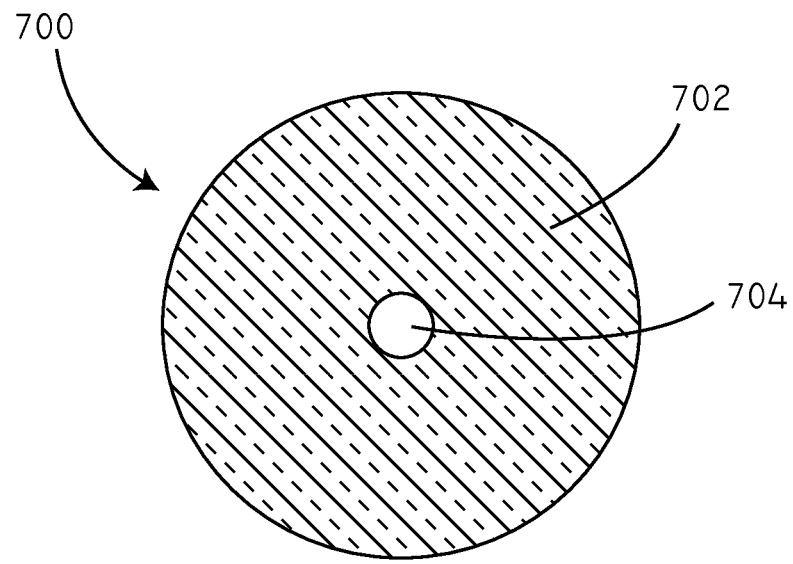
FIG. 7 is a cross-sectional schematic view of a spacing element in accordance with various embodiments herein.

Wound packing devices herein can include one or more fittings to facilitate attachment and/or removal of segments that include spacing elements so that the total amount of spacing elements or the volume of spacing elements can be easily adjusted. Referring now to FIG. 6, a wound packing device 600 is shown in accordance with various embodiments of the invention. The wound packing device 600 can include a plurality of spacing elements 602 and a connector 604. The connector 604 can include a first branch 612, a second branch 614, and a third branch 616. The wound packing device 600 can include fittings 620. Manipulation of the fittings 620 can allow the branches to be easily removed, or reattached after being removed. The fittings 620 can take on various forms. In some embodiments the fittings 620 can include a pair of threaded elements that fit together. In some embodiments, the fittings 620 can include a compression tube fitting (e.g. SWAGELOK fitting), a luer taper fitting, threaded fittings or the like. Other fittings include couplers, 3-way joints (e.g. "T's), 4-way joints (e.g. crosses) and end caps Referring now to FIG. 7, a cross-sectional schematic view of a spacing element 700 is shown in accordance with various embodiments herein. The spacing element 700 can include a core portion 702 of material that can be effective to absorb exudate. In some embodiments, the spacing element 700 is swellable. In some embodiments, the spacing element 700 can be comprised of a porous material for the core portion 702. In some embodiments, the spacing element 700 includes a fluid sequestering material. The spacing element 700 can define a central channel or lumen 704. The connector (not shown in this view) can pass through the lumen 704.

The terms "absorbent" or "absorbing" materials as used herein includes materials that are capable of adsorbent, adsorbing, retention or retaining of a fluid. Materials of the core portion can include hydrophilic absorbent polymers such as polyacrylic acid, polyacrylamides, polysaccharides (e.g. alginates), terpolymers (for example copolymers of lactide, glycolide and caprolactone), hydrogels, PEG, PVA, poly(vinyl pyrrolidone) (PVP), poly(hydroxyethylmethacrylate), hyaluronic acid and the like. In some embodiments, the hydrophilic absorbent polymers may be cross-linked. In some embodiments, the core portion can include a polyurethane foam. In other embodiments, the core portion can include hygroscopic agents that promote absorption of water.

In some embodiments, the surface of the spacing elements can be chemically modified in order to change the characteristics of the surface of the spacing elements. By way of example, in some embodiments, a modifying compound can be covalently bonded to the surface of the spacing elements. It will be appreciated that there are many different techniques through which a modifying compound could be covalently bonded to the surface of the spacing elements. One approach can be to use a compound with a thermoreactive group which can covalently bond to the surface after being activated by application of heat. Another exemplary approach can be to use a compound with a photoreactive group which can covalently bond to the surface after being activated.

Photoreactive groups respond to specific applied external stimuli to undergo active specie generation with resultant covalent bonding to an adjacent chemical surface. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. Nos. 5,002,582; 5,637,460; 5,714,360; and 6,077,698, the disclosures of which are incorporated herein by reference. Further examples of such agents are described in U.S. Publ. Pat. App. No. 2012/0046384, the content of which is herein incorporated by reference. One example of such a modification would be to provide the surface with lubricious characteristics. This can be achieved by modifying the surface of the spacing elements to have highly hydrophilic properties, such as that provided by PVP or polyacrylamide. As such, a photo-PVP compound (a compound including a photoreactive group and PVP) or a photo-polyacrylamide (a compound including a photoreactive group and polyacrylamide) could be used to modify the surface of the spacing element. Methods for the preparation of photo-PVP are described in U.S. Pat. No. 5,414,075, the content of which is herein incorporated by reference. Methods for the preparation of photo-polyacrylamide are described in U.S. Pat. No. 6,007,833, the content of which is herein incorporated by reference.

Exemplary photoreactive groups that can be pendent from the coatings, materials, or surfaces of the wound packing device, include those described in U.S. Pat. No. 5,414,075 and in U.S. patent application Ser. No. 13/490,994 (to Swan et al. and filed Jun. 7, 2012), the disclosures of which is incorporated herein by reference.

This material includes a chemical backbone having attached to it one or more first latent reactive groups and one or more second latent reactive groups, each of the first and second latent reactive groups being attached to the backbone in such a manner that, upon activation of the latent reactive groups in the presence of a support surface, a) the first latent reactive groups are capable of covalently bonding to the support surface, and b) upon bonding of the first latent reactive groups to the surface, the second latent reactive groups are; i) restricted from reacting with either a spacer or the support surface, ii) capable of reverting to their inactive state, and iii) upon reverting to their inactive state, are thereafter capable of being reactivated in order to later bind a target molecule, thereby attaching the target molecule to the surface.

In a particularly preferred embodiment, the chemical backbone of such a multifunctional reagent is a single tetrahedral carbon atom. Attached to the central carbon, in this embodiment, are four identical latent reactive groups, in the form of photoreactive groups, each attached via identical spacer chains. Upon exposure to a suitable light source, each of the latent reactive groups are subject to activation.

By virtue of conformational and/or steric constraints that the reagent imposes on itself (hence "restrained"), both by the tetrahedral nature of the central carbon, as well as the physical-chemical nature of the spacer chains themselves (e.g., their length, reactivity, and flexibility), the reagent is restricted, in that a maximum of three of the four activated latent reactive groups on any given preferred reagent molecule are able to attach to the support surface. The remaining unreacted group(s) are thus able to revert to their inactive state. In a subsequent step, the unreacted group(s) can be reactivated in the presence of a target molecule, in order to covalently bond the target molecule to the surface.

The reagent of the present invention involves a chemical backbone having attached to it one or more first latent reactive groups capable of attaching to a surface, and one or more second latent reactive groups capable of attaching to a target molecule intended for immobilization. Chemically, the first and second latent reactive groups, and respective spacers, can be the same or different.

In situations in which all latent reactive groups and spacers are chemically, or at least functionally, the same, the distinction between first and second latent reactive groups may actually be accomplished at the time of the first activation step, i.e., those groups that are activated and attach to the surface will be considered "first" latent reactive groups, and those that remain unreacted (whether or not they have been activated) will be considered "second" latent reactive groups.

The first and second latent reactive groups are preferably attached to the backbone by spacer chains in such a manner that, upon activation of the latent reactive groups in the presence of a support surface, the first latent reactive groups are capable of covalently bonding to the surface. The second latent reactive groups are thereby conformationally restricted, thus preventing reaction with either their spacers, other restricted reagents of the same type, or the support surface. In addition, after the first activation step and removal of the activating stimulus (e.g., illumination source), the second latent reactive groups are capable of reverting to their inactive state and can thereafter be activated (or reactivated, as the case may be) to covalently bond a target molecule.

The following diagram depicts the concept of the preferred tetrahedral core structure, as exemplified by the empirical formula $X(Y)_4(Z)_4$, shown below as Formula I:

FORMULA I

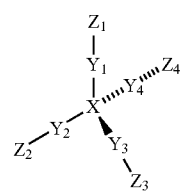

In Formula I:

X=the chemical backbone;

$Y_1$, $Y_2$, $Y_3$, $Y_4$=optional spacers; and $Z_1$, $Z_2$, $Z_3$, $Z_4$=latent reactive groups.

In an embodiment, the invention provides a core molecule containing four dimethyleneoxy groups bonded as spacers to a central tetrahedral carbon atom, the carbon atom serving in this instance as the chemical backbone. The backbone, spacers, and latent reactive groups are described herein, for the sake of simplicity, as being distinct portions of the reagent of the present invention. In the chemical synthesis of a reagent however, these portions will rarely be provided as three independent precursors. Instead, and most often, the portion referred to herein as the spacer will be formed as the result of the reaction between two molecules, one that contains the core molecule and another that contains the latent reactive group.

By virtue of the physical and chemical properties of the photoreactive groups and the methylene group spacers, together with the conformational restrictions provided by the tetrahedral carbon backbone, the reagent is able to attach up to three of its photoreactive groups to a surface upon photoactivation. Being conformationally restricted, and thus unable to interact with the support surface or the spacers, any remaining photoreactive group(s) are able to return to their inactive states upon removal of fight, once again being capable of activation by subsequent illumination.

In addition to reagents of the particularly preferred embodiment, containing a central carbon atom, reagents of the present invention can be prepared having any suitable chemical (e.g., organic and/or inorganic) backbone structure, including those that employ a single atom, such as silicon, nitrogen, phosphorus, and any other atom with four or more bonds nonplanar with respect to one another.

Also, molecules having conformationally restricted ring structures (such as inositol, i.e., hexahydroxy cyclohexane) can be derivatized with latent reactive groups in a manner analogous to that described herein for pentaerythritol, to provide latent reactive groups in both axial and equatorial positions. Other polyhydroxylated compounds such as mono- and di-saccharides, and cyclodextrins, are suitable as well, in that they offer alternative opportunities to create other multisubstituted reagents having varying placements and densities of latent reactive groups.

Contact with a support surface and activation of the latent reactive groups will result in covalent bond formation through at least one latent reactive group, with at least one other latent reactive group being conformationally restricted and thus unable to react at the surface.

Spacers useful in the reagent of the present invention can be bonded to the tetrahedral atom and can be of any suitable length and structure. A "spacer", as used herein, refers to that region of a reagent between a latent reactive group and a chemical backbone. The use of spacers is optional, and would not be necessary, for instance, for such compounds as acylated derivatives of tetraphenylmethane having the structure shown below as Formula II:

FORMULA II

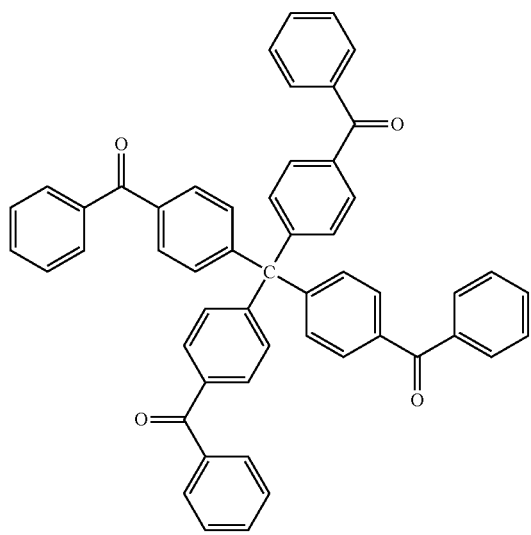

A "latent reactive group", as used herein, refers to a chemical group that responds to an applied external energy source in order to undergo active specie generation, resulting in covalent bonding to an adjacent chemical structure (e.g., an abstractable hydrogen). Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones such as acetophenone and benzophenone, or their derivatives, are preferred, since these functional groups, typically, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are suitable.

A linking agent suitable for use in the present material is described in U.S. Pat. No. 5,714,360, the disclosure of which is incorporated herein by reference.

A chemical linking agent including a di- or higher functional photoactivatable charged compound can be employed. This linking agent provides at least one group that is charged under the conditions of use in order to provide improved water solubility. The agent further provides two or more photoactivatable groups in order to allow the agent to be used as a cross-linking agent in aqueous systems. In an embodiment, the charge is provided by the inclusion of one or more quaternary ammonium radicals, and the photoreactive groups are provided by two or more radicals of an aryl ketone such as benzophenone.

In a preferred embodiment, the invention provides a linking agent of the general formula: X—Y—X; wherein each X, independently, is a radical containing a photoreactive group and Y is a radical containing, inter alia, one or more charged groups. In such an embodiment, the number and/or type of charged group(s) is sufficient to provide the molecule with sufficient aqueous solubility to allow the agent to be used (i.e., applied to a surface and activated) in a solvent system having water as a major component.

In an embodiment, Y contains one or more nitrogen-containing (e.g., quaternary ammonium) groups. For example, Y contains a linear or heterocyclic radical selected from the group consisting of:

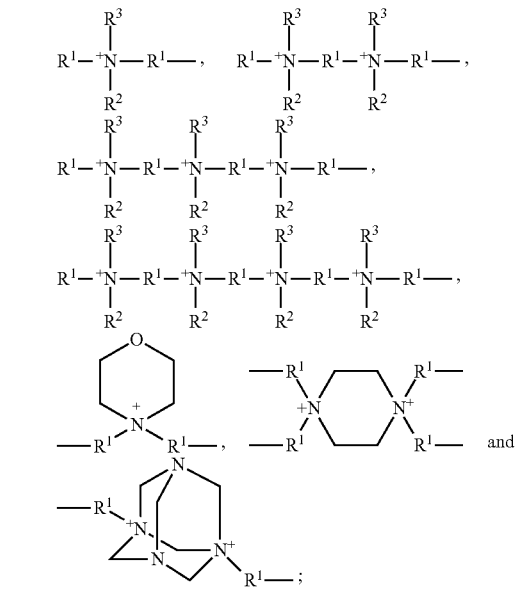

wherein each $R^1$ independently is a radical containing an alkylene, oxyalkylene, cycloalkylene, arylene, or aralkylene group, each $R^2$ independently is a radical containing an alkyl, oxyalkyl, cycloalkyl, aryl, or aralkyl group, and each $R^3$ independently is either a non-bonding pair of electrons, a hydrogen atom, or a radical of the same definition as $R^2$, in which the $R^1$, $R^2$ and $R^3$ groups can contain noninterfering heteroatoms such as O, N, S, P and the like, and/or noninterfering substituents such as halo (e.g., Cl) and the like.

In an embodiment, one or more $R^2$ radicals contains an aralkyl group in the form of a photoactivatable aryl ketone. These groups, in addition to the two photoactivatable groups provided by the above-defined X groups, can be used to provide the "triphoto", "tetraphoto" and higher order photoactivatable groups described herein. The use of three or more total photoreactive groups provides the linking agent with further ability to cross-link the agent to a target molecule and/or to a surface.

In yet another preferred embodiment, the $R^2$ and $R^3$ groups of the above linear radicals can, in effect, be fused (e.g., an $R^2$ and an $R^3$ on a single N atom, or a suitable combination of $R^2/R^3$ groups on adjacent N atoms) in order to form heterocyclic structures other than those exemplified above. The specific choice and relationship between R groups in a linking agent of the present invention is not critical, so long as the linking agent provides two or more photoactivatable groups and retains sufficient water solubility for its intended use.

Linking Agent

A water-soluble, linking agent suitable for use as the present device is described in U.S. patent application Ser. No. 13/074,537 (Kurdyumov et al.; filed Mar. 29, 2011), the disclosure of which is incorporated herein by reference.

The linking agent can have the formula $Photo^1$-LG-$Photo^2$, wherein $Photo^1$ and $Photo^2$, independently, represent at least one photoreactive group and LG represents a linking group. In one embodiment, one or more photoreactive groups include an aryl ketone. In a more particular embodiment, one or more photoreactive groups include benzophenone.

In one embodiment, the linking group includes one or more silicon atoms or one or more phosphorus atoms, wherein each photoreactive group is independently bonded to the linking group by a covalent linkage that includes at least one heteroatom. In one embodiment, at least one heteroatom is selected from oxygen, nitrogen, selenium, sulfur, or a combination thereof. In one embodiment, at least one photoreactive group, heteroatom and linking group form an ether or an amine.

In a more particular embodiment, the linking group includes one silicon atom covalently bonded to at least two photoreactive groups. In another embodiment, the linking group includes at least two silicon atoms. In another embodiment, the linking group has the formula Si—Y—Si, wherein Y represents a linker that can be null, an amine, ether, linear or branched $C_1$-$C_{10}$ alkyl, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30.

In another embodiment, the linking group includes one or more phosphorester bonds and/or one or more phosphoramide bonds wherein one or more phosphorester and/or one or more phosphoramide bonds form a covalent bond with at least one photoreactive group, such that the linking group includes at least two photoreactive groups. In one embodiment, the linking group is covalently attached to three photoreactive groups, wherein each photoreactive group is covalently bonded to the linking group by a phosphorester or phosphoramide bond. In another embodiment, the linking group includes at least one phosphorus atom with a phosphorus-oxygen double bond (P=O), wherein at least one photoreactive group is bonded to at least one phosphorus atom. In yet another embodiment, the linking group includes one phosphorus atom with a phosphorus-oxygen double bond (P=O), wherein at least two or three photoreactive groups are covalently bonded to the phosphorus atom. In another embodiment, the linking group includes at least two phosphorus atoms, wherein at least one phosphorus atom includes a phosphorus-oxygen double bond (P=O), and at least one or at least two photoreactive groups are covalently bonded to each phosphorus atom.

The linking agent includes one or more photoreactive groups and a linking group, wherein each photoreactive group is independently attached to the linking group by a linkage. In other embodiments, the linking agent includes two or more photoreactive groups. In still other embodiments, the linking agent includes three or more photoreactive groups.

The linking agent includes one or more photoreactive groups attached to a linking group. The linking agent can be represented by the formula $Photo^1$-LG-$Photo^2$, wherein $Photo^1$ and $Photo^2$ independently represent at least one photoreactive group and LG represents a linking group. The term "linking group" as used herein, refers to a segment or group of molecules configured to connect two or more molecule to each another, wherein the linking group is capable of degrading under one or more conditions. In one embodiment, the linking group includes at least one silicon atom. In another embodiment, the linking group includes at least one phosphorus atom.

The term "linking group" as used herein, refers to a moiety configured to connect one molecule to another, wherein the linking group is capable of cleavage under one or more conditions. The term "biodegradable" as used herein, refers to degradation in a biological system, and includes for example, enzymatic degradation or hydrolysis. It should be noted that the term "degradable" as used herein includes both enzymatic and non-enzymatic (or chemical) degradation. It is also understood that hydrolysis can occur in the presence of or without an acid or base. In one embodiment, the linking agent is water soluble. In another embodiment, the linking agent is not water soluble.

In addition to providing a bond, the linking group can function as a spacer, for example, to increase the distance between the photoreactive groups of the linking agent. For example, in some instances it may be desirable to provide a spacer to reduce steric hindrance that may result between the photoreactive groups, which could interfere with the ability of the photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

As described herein, one or more photoreactive groups can be bonded to a linking group by a linkage. In one embodiment, the linkage between the photoreactive group and the linking group includes at least one heteroatom, including, but not limited to oxygen, nitrogen, selenium, sulfur or a combination thereof. In one embodiment, a photoreactive group, linking group and heteroatom form an ether ($R^1$—O—$R^2$), wherein $R^1$ is a photoreactive group and $R^2$ is a linking group. In another embodiment, a photoreactive group, linking group and heteroatom form an amine,

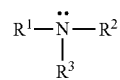

wherein $R^1$ is a photoreactive group, $R^2$ is a linking group, and $R^3$ is hydrogen, aryl or alkyl, a photoreactive group, or a hydroxyl or salt thereof. In one embodiment, $R^3$ is cyclic, linear or branched, saturated or unsaturated, aromatic or heteroaromatic, or a combination thereof. The stability of the ether and/or amine linkage can be influenced depending upon the size (e.g., chain length, branching, bulk, etc.) of the substituents. For example, bulkier substituents will generally result in a more stable linkage (i.e., a linking agent that is slower to degrade in the presence of water and/or acid).

In one embodiment, the linking group includes one or more silicon atoms. In a particular embodiment, the linking group includes one silicon atom (which can be referred to as a monosilane) covalently bonded to at least two photoreactive groups. In another embodiment, the linking group includes at least two silicon atoms (which can be referred to as a disilane). In one embodiment, the linking group can be represented by the formula Si—Y—Si, wherein Y represents a linker that can be null (e.g., the linking group includes a direct Si—Si bond), an amine, ether, linear or branched $C_1$-$C_{10}$ alkyl, or a combination thereof. In one embodiment, Y is selected from O, $CH_2$, $OCH_2CH_2O$, $O(CH(CH3)CH_2O)_n$, and $O(CH_2CH_2O)_n$, wherein n is an integer between 1 and 5, between 1 and 10, between 1 and 15, between 1 and 20, between 1 and 25, or between 1 and 30. One embodiment of a disilane linking agent is shown below

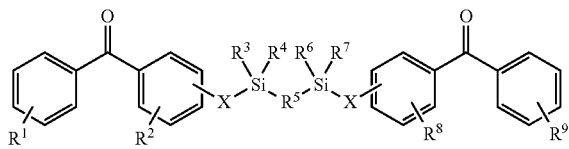

wherein $R^1$, $R^2$, $R^8$ and $R^9$ can be any substitution, including, but not limited to H, alkyl, halide, hydroxyl, amine, or a combination thereof; $R^3$, $R^4$, $R^6$ and $R^7$ can be alkyl, aryl or a combination thereof; $R^5$ can be any substitution, including but not limited to O, alkyl or a combination thereof; and each X, independently, can be O, N, Se, S, or alkyl, or a combination thereof. One specific embodiment is shown below:

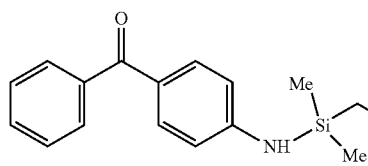

In one embodiment, the linking agent can be represented by the formula

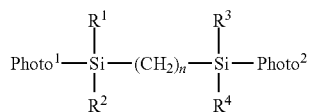

wherein Photo$^1$ and Photo$^2$, independently, represent one or more photoreactive groups and n is an integer between 1 and 10, wherein the linking agent comprises a covalent linkage between at least one photoreactive group and the linking group, wherein the covalent linkage between at least one photoreactive group and the linking group is interrupted by at least one heteroatom. In general, a longer hydrocarbon chain between the two silicon atoms will tend to increase the flexibility of the linking agent and may facilitate crosslinking between a greater number of polymers than a linking agent with a shorter carbon chain, since the photoreactive groups can react with polymers located farther apart from one another. In the formula shown above, $R^1$, $R^2$, $R^3$, $R^4$ are independently alkyl or aryl, including, but not limited to cyclic, linear or branched, saturated or unsaturated, aromatic or heteroaromatic, or a combination thereof. In a more particular embodiment, $R^1$-$R^4$ are independently phenyl, methyl, ethyl, isopropyl, t-butyl, or a combination thereof. In another embodiment, $R^1$-$R^4$ can also be, independently, a photoreactive group. In yet another embodiment, $R^1$-$R^4$ can also be, independently, hydroxyl or salt thereof. In one embodiment, the hydroxyl salt includes a counterion that is lithium, sodium, potassium, or a combination thereof.

In another embodiment, the linking agent can be represented by the formula

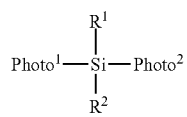

wherein Photo$^1$ and Photo$^2$, independently, represent one or more photoreactive group, wherein the linking agent comprises a covalent linkage between at least one photoreactive group and the linking group, wherein the covalent linkage between at least one photoreactive group and the linking group is interrupted by at least one heteroatom; $R^1$ and $R^2$ are independently alkyl or aryl, including, but not limited to cyclic, linear or branched, saturated or unsaturated, aromatic or heteroaromatic, or a combination thereof. In a more particular embodiment, $R^1$ and $R^2$ are independently phenyl, methyl, ethyl, isopropyl, t-butyl, or a combination thereof. $R^1$ and $R^2$ can also be, independently, a photoreactive group, wherein the linking agent comprises a covalent linkage between at least one photoreactive group and the linking group, wherein the covalent linkage between at least one photoreactive group and the linking group is interrupted by at least one heteroatom; or hydroxyl or salt thereof. In one embodiment, the hydroxyl salt includes a counterion that is lithium, sodium, potassium, or a combination thereof. One embodiment of a monosilane linking agent is shown below

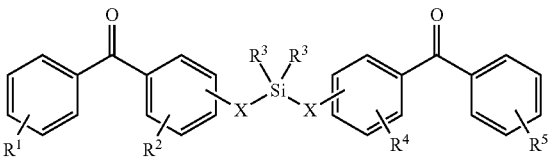

in which $R^1$ and $R^5$ can be any substitution, including, but not limited to H, halogen, amine, hydroxyl, alkyl, or a combination thereof; $R^2$ and $R^4$ can be any substitution, except OH, including, but not limited to H, alkyl or a combination thereof; $R^3$ can be alkyl, aryl or a combination thereof; and X, independently, can be O, N, Se, S, alkyl or a combination thereof.

In another embodiment, the linking group includes one or more phosphorous atoms. In one embodiment, the linking group includes one phosphorus atom (which can also be referred to as a mono-phosphorus linking group). In another embodiment, the linking agent includes two phosphorus atoms (which can also be referred to as a bis-phosphorus linking group). In one embodiment, the linking group comprises at least one phosphorus atom with a phosphorus-oxygen double bond (P=O), wherein at least one or two photoreactive groups are bonded to the phosphorus atom. In another embodiment, the linking group comprises one phosphorus atom with a phosphorus-oxygen double bond (P=O), wherein two or three photoreactive groups are covalently bonded to the phosphorus atom. In another embodiment, the linking group comprises at least two phosphorus atoms, wherein at least one phosphorus atom includes a phosphorus-oxygen double bond (P=O), and at least one or two photoreactive groups are covalently bonded to each phosphorus atom.

In a more particular embodiment, the linking agent can be represented by the formula:

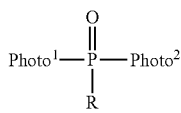

wherein $Photo^1$ and $Photo^2$, independently, represent one or more photoreactive groups, wherein the linking agent comprises a covalent linkage between at least one photoreactive group and the linking group, wherein the covalent linkage between at least one photoreactive group and the linking group is interrupted by at least one heteroatom and R is alkyl or aryl, a photoreactive group, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the linking agent can be represented by formula:

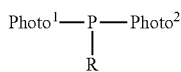

wherein $Photo^1$ and $Photo^2$ independently, represent one or more photoreactive groups, wherein the linking agent comprises a covalent linkage between at least one photoreactive group and the linking group, wherein the covalent linkage between at least one photoreactive group and the linking group is interrupted by at least one heteroatom and R is alkyl or aryl, a photoreactive group (wherein the covalent linkage between the photoreactive group and the linking group may be interrupted by at least one heteroatom), hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, R is phenyl, methyl, ethyl, isopropyl, t-butyl, or a combination thereof.

In another embodiment, the linking agent can be represented by the formula:

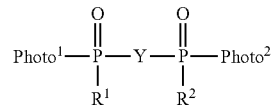

wherein $Photo^1$ and $Photo^2$, independently, represent one or more photoreactive groups, wherein the linking agent comprises a covalent linkage between at least one photoreactive group and the linking group, wherein the covalent linkage between at least one photoreactive group and the linking group is interrupted by at least one heteroatom; Y represents a linker that can be N or O (e.g., pyrophosphate), linear or branched $C_1$-$C_{10}$ alkyl, or a combination thereof; and $R^1$ and $R^2$ are independently alkyl, aryl, a photoreactive group (wherein the covalent linkage between the photoreactive group and the linking group can be interrupted by at least one heteroatom), hydroxyl or salt thereof, or a combination thereof. In one embodiment, Y is selected from O, $CH_2$, $OCH_2CH_2O$, $O(CH(CH3)CH_2O)_n$, and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof. In general, a longer hydrocarbon chain between the two phosphorus atoms will tend to increase the flexibility of the linking agent and may facilitate crosslinking between a greater number of polymers than a linking agent with a shorter carbon chain, since the reactive photoreactive groups can react with polymers located farther apart from one another. In one embodiment, Y can be O, $CH_2$, $OCH_2CH_2O$, $O(CH_2(CH3)CH_2O)_n$, and $O(CH_2CH_2O)_n$ wherein n is an integer between 1 and 5, between 1 and 10, between 1 and 15, between 1 and 20, between 1 and 25, or between 1 and 30. One embodiment is shown below

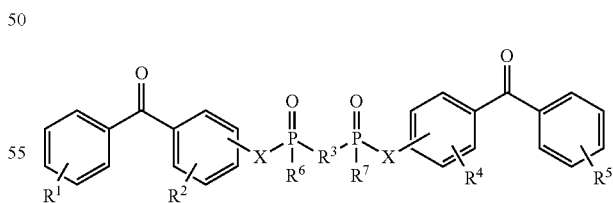

in which $R^1$, $R^2$, $R^4$ and $R^5$ can be any substitution, including but not limited to H, alkyl, halogen, amine, hydroxyl, or a combination thereof; $R^3$ can be any substitution, including but not limited to O, alkyl, or a combination thereof; $R^6$ and $R^7$ can be alkyl, aryl or a combination thereof; and each X can independently be O, N. Se, S, alkyl, or a combination thereof. In one embodiment, the linking agent includes one or more phosphorester bonds and one or more phosphoramide bonds, and can be represented by the formula:

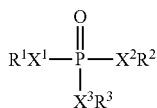

wherein X and $X^2$ are, independently, O, N, Se, S or alkyl; $R^1$ and $R^2$ are independently, one or more photoreactive groups, and $X^3$ is O, N, Se, S, alkyl or aryl; $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In one embodiment, the linking agent comprises a triphosphorester, which can be represented by the formula.

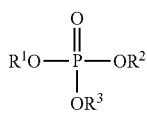

wherein $R^1$ and $R^2$ are independently, one or more photoreactive groups, and $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In another embodiment, the linking agent comprises a triphosphoramide, which can be represented by the formula.

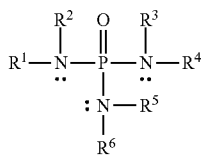

wherein $R^1$-$R^6$ are independently, a photoreactive group, a hydroxyl or salt thereof, alkyl or aryl, or a combination thereof, wherein at least two of $R^1$-$R^6$ are, independently, a photoreactive group. In one embodiment, the hydroxyl salt counterion is lithium, sodium, potassium, or a combination thereof. In a more particular embodiment, $R^1$-$R^6$ are independently cyclic, linear or branched, saturated or unsaturated, aromatic or heteroaromatic, or a combination thereof. In a more particular embodiment, $R^1$-$R^6$ are, independently, phenyl, methyl, ethyl, isopropyl, t-butyl, or a combination thereof.

The linking agent can be formed using any suitable reaction pathway. In one embodiment, the linking agent is formed by reacting a functionalized linking element with one or more, typically two or more photoreactive groups. As used herein, the term "linking element" refers to the linking group component of the linking agent before it is bonded to one or more photoreactive groups. The term "functionalized linking element" is used to indicate that the linking element includes one or more reactive functional groups. In one embodiment, the linking element includes one or more halogen functional groups. The term "halogen" refers to fluorine, chlorine, bromine, or iodine functional groups. In another embodiment, the linking element includes one or more trifluoromethanesulfonate ($CF_3SO_3$—) functional groups.

In one embodiment, the linking element includes one or more silicon atoms. In one embodiment, the linking element includes one or more halogen substituents, such as fluorine, chlorine, bromine, iodine, and combinations thereof. In another embodiment, the linking element includes at least two halogen substituents. In another embodiment, the linking element includes one or more trifluoromethanesulfonate (triflate) substituents. In another embodiment, the linking element includes at least two triflate substituents. In a more particular embodiment, the linking element includes one silicon atom with at least two halogen or triflate substituents. In another embodiment, the linking element includes at least two silicon atoms. In a more particular embodiment, the linking element includes two silicon atoms, wherein each silicon atom includes at least one halogen or triflate substituent. In one embodiment, the linking element can be represented by the formula Si—Y—Si, wherein Y represents a linker that can be null, an amine, ether, linear or branched $C_1$-$C_{10}$ alkyl, or a combination thereof, wherein each silicon atom includes at least one halogen or triflate substituent. In one embodiment, Y is selected from O, $CH_2$, $OCH_2CH_2O$, $O(CH(CH3)CH_2O)_n$, and $O(CH_2CH_2O)_n$, wherein n is an integer between 1 and 5, between 1 and 10, between 1 and 15, between 1 and 20, between 1 and 25, or between 1 and 30.

In one embodiment, the linking element can be represented by the formula

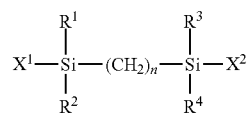

wherein $X^1$ and $X^2$ are independently halogen, such as fluorine, chlorine, bromine, iodine; trifluoromethanesulfonate; or a combination thereof and n is an integer between 1 and 10. $R_1$-$R_4$ are independently alkyl or aryl, including, but not limited to cyclic, linear or branched, saturated or unsaturated, aromatic or heteroaromatic, or a combination thereof. In a more particular embodiment, $R^1$-$R^4$ are independently phenyl, methyl, ethyl, isopropyl, t-butyl, or a combination thereof. In another embodiment, $R^1$-$R^4$ can also be, independently, halogen. In yet another embodiment, $R^1$-$R^4$ can also be, independently, hydroxyl or salt thereof. In one embodiment, the hydroxyl salt includes a counterion that is lithium, sodium, potassium, or a combination thereof.

In another embodiment, the linking element can be represented by the formula

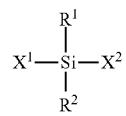

wherein $X^1$ and $X^2$ are independently halogen; such as fluorine, chlorine, bromine, and iodine; or trifluoromethanesulfonate; $R^1$ and $R^2$ are independently alkyl or aryl, including, but not limited to cyclic, linear or branched, saturated or unsaturated, aromatic or heteroaromatic, or a combination thereof. In a more particular embodiment, $R^1$ and $R^2$ are independently phenyl, methyl, ethyl, isopropyl, t-butyl, or a combination thereof. $R^1$ and $R^2$ can also be, independently, halogen, hydroxyl or hydroxyl salt. In one embodiment, the hydroxyl salt includes lithium, sodium, potassium, or a combination thereof as a counterion.

In another embodiment, the linking element includes one or more phosphorous atoms. In one embodiment, the linking element comprises at least one phosphorus atom with a phosphorus-oxygen double bond (P=O), wherein at least one halogen or trifluoromethanesulfonate substituent is bonded to at least one phosphorus atom. In another embodiment, the linking element comprises one phosphorus atom with a phosphorus-oxygen double bond (P=O), wherein two or three halogen or trifluoromethanesulfonate substituents are, independently, covalently bonded to the phosphorus atom. In another embodiment, the linking element comprises at least two phosphorus atoms, wherein at least one phosphorus atom includes a phosphorus-oxygen double bond (P=O), and at least one or two halogen or trifluoromethanesulfonate substituents are covalently bonded to each phosphorus atom. In a more particular embodiment, the linking element comprises two phosphorus atoms.

In a more particular embodiment, the linking element can be represented by the formula

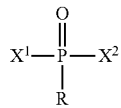

wherein $X^1$ and $X^2$ are independently halogen; such as fluorine, chlorine, bromine, and iodine; or trifluoromethanesulfonate; and R is alkyl or aryl, halogen, hydroxyl or a hydroxyl salt, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the linking element can be represented by formula:

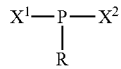

wherein $X^1$ and $X^2$ are independently halogen, such as fluorine, chlorine, bromine, and iodine; or trifluoromethanesulfonate and R is alkyl or aryl, halogen, trifluoromethanesulfonate, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

In another embodiment, the linking element can be represented by the formula:

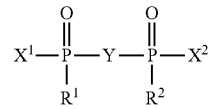

wherein $X^1$ and $X^2$ are independently halogen, such as fluorine, chlorine, bromine, and iodine; or trifluoromethanesulfonate, Y represents a linker that can be null, an amine, an ether, linear or branched $C_1$-$C_{10}$ alkyl, or a combination thereof; and $R^1$ and $R^2$ are independently alkyl, aryl, halogen, hydroxyl or salt thereof, or a combination thereof. In one embodiment, Y is selected from O, $CH_2$, $OCH_2CH_2O$, $O(CH(CH3)CH_2O)_n$, and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

Water-Soluble, Degradable Linking Agent

A water-soluble, degradable linking agent suitable for use in the present polymeric medical device is described in U.S. Patent Application Nos. 61/285,345 and 61/358,464, the disclosure of which is incorporated herein by reference.

Described in this section is a linking agent that includes a core molecule with one or more charged groups; and one or more photoreactive groups covalently attached to the core molecule by one or more degradable linkers. In one embodiment, the linking agent includes a non-polymeric core molecule. In one embodiment, the non-polymeric core molecule is a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof. In one embodiment, one or more degradable linkers comprise an amide, an ester, a thiocarbamate, or a combination thereof. In one embodiment, one or more photoreactive group is an aryl ketone, including, for example, acetophenone, benzophenone, anthraquinone, anthrone, anthrone-like heterocycles, substituted derivatives thereof, or a combination thereof. In one embodiment, one or more charged groups are negatively charged, including, for example, an organic acid selected from sulfuric acid, sulfonic acid, carboxylic acid, phosphoric acid, phosphonic acid, or a combination thereof. In another embodiment, one or more charged groups are positively charged, for example, a quaternary ammonium salt.

Described herein is a water-soluble, degradable linking agent. The degradable linking agent includes one or more photoreactive groups, one or more charged groups, and one or more degradable linkers configured to operably attach one or more photoreactive groups to one or more negatively charged groups. In one embodiment, the linking agent includes a core having one or more charged groups attached directly or indirectly thereto and one or more photoreactive groups attached to the non-polymeric core by one or more degradable linkers.

The degradable linking agent includes one or more photoreactive groups attached to one or more charged groups by a degradable linker. In a more particular embodiment, the degradable linking agent includes a core molecule to which the charged groups and the photoreactive groups can be independently attached. In one embodiment, the degradable linking agent includes a non-polymeric core molecule. The term "degradable linker" as used herein, refers to a segment configured to connect one part of the linking agent to another, wherein the linker is capable of cleavage under one or more conditions. The term degradable as used herein also encompasses "biodegradable linkers." The term "biodegradable" as used herein, refers to degradation in a biological system, and includes for example, enzymatic degradation or hydrolysis. It should be noted that the term "degradable" as used herein includes both enzymatic and non-enzymatic (or chemical) degradation. In one embodiment, the degradable linker comprises one or more degradable linkages such as an amide, an ester, a thiocarbamate, or combinations thereof.

In addition to providing a degradable segment, the degradable linker can function as a spacer, to increase the distance between one or more photoreactive groups and the core molecule. For example, in some instances it may be desirable to provide a spacer to reduce steric hindrance that may result between the core molecule and one or more photoreactive groups that could interfere with the ability of one or more photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

A degradable linking agent can be represented by the formula:

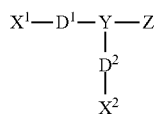

wherein $X^1$ and $X^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $D^1$ and $D^2$ are, independently, degradable segments, including, for example, degradable segments that include an amide, an ester, a thiocarbamate, or a combination thereof; Y represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof; and Z represents one or more charged groups, including, for example, one or more negatively charged groups such as an organic acid salt, including but not limited to sulfuric acid, sulfonic acid, carboxylic acid, phosphoric acid, phosphonic acid, or a combination thereof; one or more positively charged groups, for example, a quaternary ammonium salt, or a combination thereof.

In the formula shown above, the two or more photoreactive groups ($X^1$ and $X^2$) are discrete. As used herein, the term "discrete" means that the two or more photoreactive groups are distinct from each other, as compared to a bifunctional photoreactive agent, that can include two or more photoreactive moieties, such as a conjugated cyclic diketone wherein each ketone group of the diketone is adapted to serve as a photoreactive moiety capable of being activated in order to provide a free radical. It is also understood that the first and second photoreactive groups and/or the first and second degradable linkers may or may not be the same. For example, in one embodiment, the photoreactive groups ($X^1$ and $X^2$) are the same or identical. In another embodiment, the photoreactive groups ($X^1$ and $X^2$) are not the same. In one embodiment, the degradable linker ($D^1$ and $D^2$) are the same or identical. In another embodiment, the degradable linker ($D^1$ and $D^2$) are not the same. In one embodiment, the photoreactive groups include one or more first photoreactive groups adapted to attach the linking agent to a surface and one or more second photoreactive groups adapted to initiate photopolymerization.

In one embodiment, the degradable linker is a biodegradable linker that includes an amide bond (also referred to as a peptide bond, or peptide linker). A peptide bond can be cleaved by amide hydrolysis (the addition of water) by enzymatic and non-enzymatic reactions. Proteolysis refers to amide hydrolysis catalyzed by an enzyme. The term "protease" refers to an enzyme that conducts proteolysis. Examples of enzymes capable of hydrolyzing a peptide bond include, but are not limited to, acylase, amidohydrolase, deaminase, trypsin, and alpha-chymotrypsin.

A nonlimiting example of a degradable linker with a peptide bond can be represented by formula I:

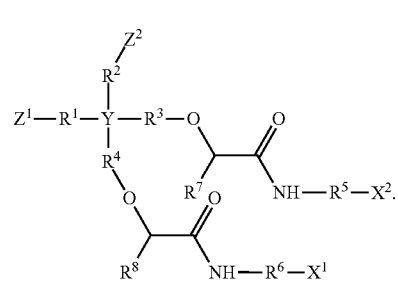

wherein $X^1$ and $X^2$ include, independently, one or more photoreactive groups, including, but not limited to, aryl ketone photoreactive groups, such as acetophenone, benzophenone, anthraquinone, anthrone, anthrone-like heterocycles, their substituted derivatives or a combination thereof; Y represents a core molecule, which can be polymeric or non-polymeric, including for example, non-polymeric molecules such as a hydrocarbon, including linear, branched or cyclic; aromatic or non-aromatic; monocyclic, polycyclic, carbocyclic or heterocyclic; benzene or a derivative thereof; or combinations thereof; $Z^1$ and $Z^2$ represent, independently, one or more charged groups, including positively and negatively charged groups, for example a negatively charged group that includes an organic acid salt, including but not limited to sulfuric acid, sulfonic acid, carboxylic acid, phosphoric acid, phosphonic acid, or a combination thereof; one or more positively charged groups, for example, a quaternary ammonium salt; or a combination thereof. $R^1$, $R^2$, $R^3$, and $R^4$ are, independently, spacer elements that can be null, a heteroatom, alkyl or aryl, including, but not limited to cyclic, linear or branched, saturated or unsaturated, aromatic or heteroaromatic, or a combination thereof; $R^5$ and $R^6$ are, independently, spacer elements that can be null, alkyl or aryl, including, but not limited to cyclic, linear or branched, saturated or unsaturated, aromatic or heteroaromatic, or a combination thereof; and $R^7$ and $R^8$ are, independently substituents that can be hydrogen, alkyl or aryl, including, but not limited to cyclic, linear or branched, saturated or unsaturated, aromatic or heteroaromatic, or a combination thereof.

More specific examples of a degradable linker that includes a degradable amide bond include those shown in formulae II and III:

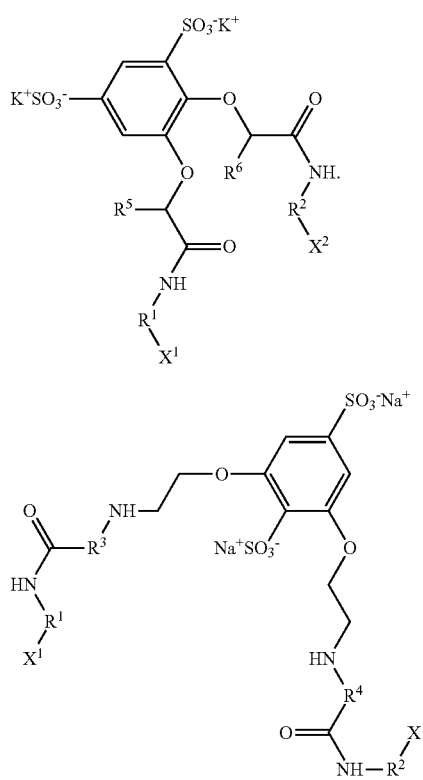

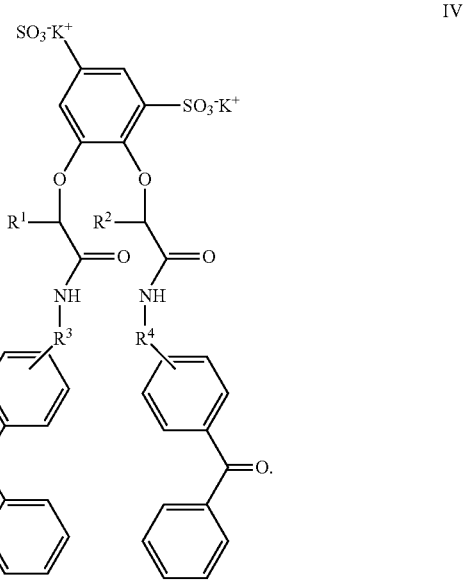

wherein $X^1$ and $X^2$ include, independently, one or more photoreactive groups, including, but not limited to aryl ketone photoreactive groups, such as acetophenone, benzophenone, anthraquinone, anthrone, anthrone-like heterocycles, their substituted derivatives or a combination thereof; and $R^1$, $R^2$, $R^3$, and $R^4$ are, independently, spacer elements, which can be null, alkyl or aryl, including, but not limited to cyclic, linear or branched, saturated or unsaturated, aromatic or heteroaromatic, or a combination thereof; and $R^5$ and $R^6$ are, independently substituents that can be hydrogen, alkyl or aryl, including, but not limited to cyclic, linear or branched, saturated or unsaturated, aromatic or heteroaromatic, or a combination thereof.

More specific examples of linkers with degradable peptide bonds are shown in formula IV, below, wherein $R^1$ and $R^2$ are, independently, substituents that can be hydrogen, alkyl or aryl, including, but not limited to cyclic, linear or branched, saturated or unsaturated, aromatic or heteroaromatic, or a combination thereof; and $R^3$ and $R^4$ are, independently, spacer elements, which can be null, alkyl or aryl, including, but not limited to cyclic, linear or branched, saturated or unsaturated, aromatic or heteroaromatic, or a combination thereof.

In another embodiment, the degradable linking agent includes one or more ester bonds. Esters can be hydrolyzed to the parent carboxylic acid and an alcohol under acidic or basic conditions. An example of a linker with a degradable ester bond is shown in formula V and VI.

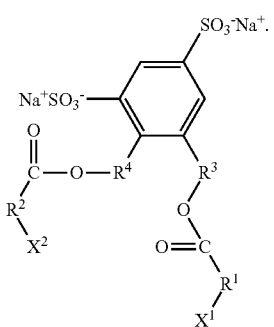

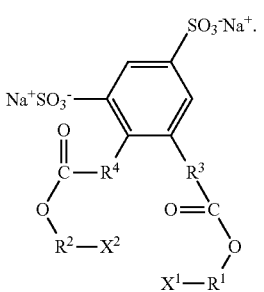

wherein $X^1$ and $X^2$ include, independently, one or more photoreactive groups, including but not limited to aryl ketone photoreactive groups, such as acetophenone, benzophenone, anthraquinone, anthrone, anthrone-like heterocycles, their substituted derivatives or a combination thereof; and $R^1$, $R^2$, are, independently, spacer elements, which can be null, alkyl or aryl, including, but not limited to cyclic, linear or branched, saturated or unsaturated, aromatic or heteroaromatic, or a combination thereof. $R^3$ and $R^4$ are, independently, spacer elements, which can be null, a heteroatom, including, but not limited to O, N or S, alkyl or aryl, including, but not limited to cyclic, linear or branched, saturated or unsaturated, aromatic or heteroaromatic, or a combination thereof.

In another embodiment, the degradable linking agent includes one or more thiocarbamate bonds. Thiocarbamates are carbamates in which the C=O group has been replaced by a C=S group. One example of a degradable linker with a thiocarbamate bond can be represented by formula VII:

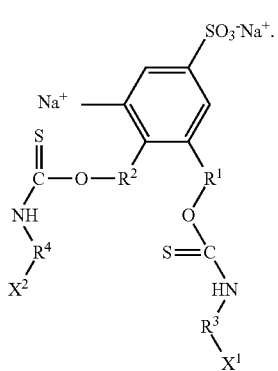

VII wherein $X^1$ and $X^2$ include, independently, one or more photoreactive groups, including but not limited to aryl ketone photoreactive groups, such as acetophenone, benzophenone, anthraquinone, anthrone, anthrone-like heterocycles, their substituted derivatives or a combination thereof; $R^1$ and $R^2$ are, independently, spacer elements, which can be null, a heteroatom, including, but not limited to O, N or S, alkyl or aryl, including, but not limited to cyclic, linear or branched, saturated or unsaturated, aromatic or heteroaromatic, or a combination thereof; and $R^3$ and $R^4$ are, independently, spacer elements, which can be null, alkyl or aryl, including, but not limited to cyclic, linear or branched, saturated or unsaturated, aromatic or heteroaromatic, or a combination thereof.

Figure 8:
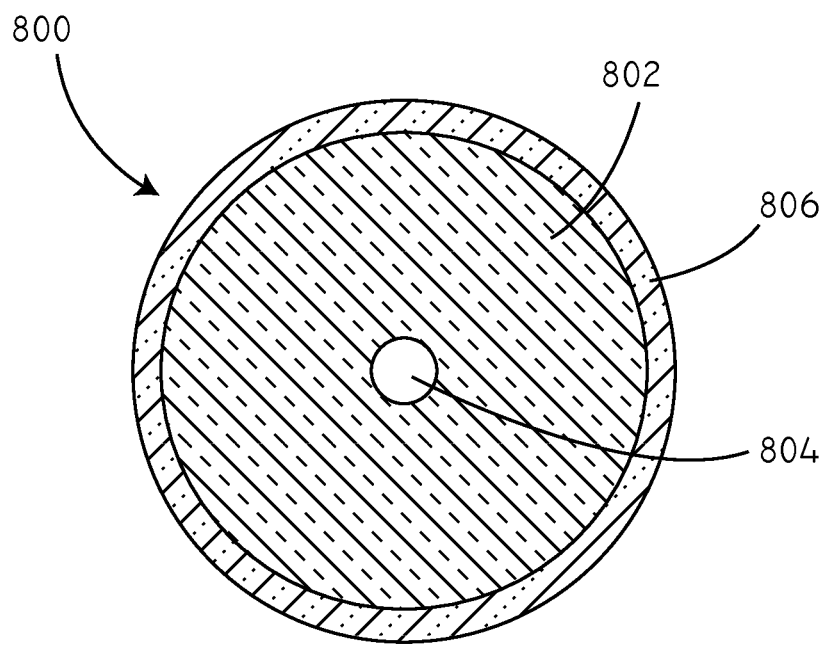
FIG. 8 is a cross-sectional schematic view of a spacing element in accordance with various embodiments herein.

In some embodiments, a separate material can be disposed in a layer over the first material or portion. Referring now to FIG. 8, a cross-sectional schematic view of a spacing element 800 is shown in accordance with various embodiments herein. The spacing element 800 can include an inner portion 802 including a first material. The inner portion 802 can define a central lumen 804. The spacing element 800 can also include an outer portion 806 including a second material. The outer portion 806 can be continuous or discontinuous over the surface of the spacing element 800 (for example, the outer portion can have discontinuities such as pores or openings). The outer portion 806 can include a water permeable material. The outer portion 806 can include a lubricious coating. In some embodiments the outer portion 806 can include a layer of flashspun high-density polyethylene fibers. In some embodiments the outer portion 806 can include a layer of expanded polytetrafluoroethylene (ePTFE). In some embodiments, the outer portion 806 can include a layer of graphene. In some embodiments, the outer portion 806 can include a layer of graphene with a modifying compound covalently bonded thereto. For example, a linking agent can be covalently bonded to the graphene and to another compound having desired functional properties thereby providing the graphene surface with those properties.

Figure 9:
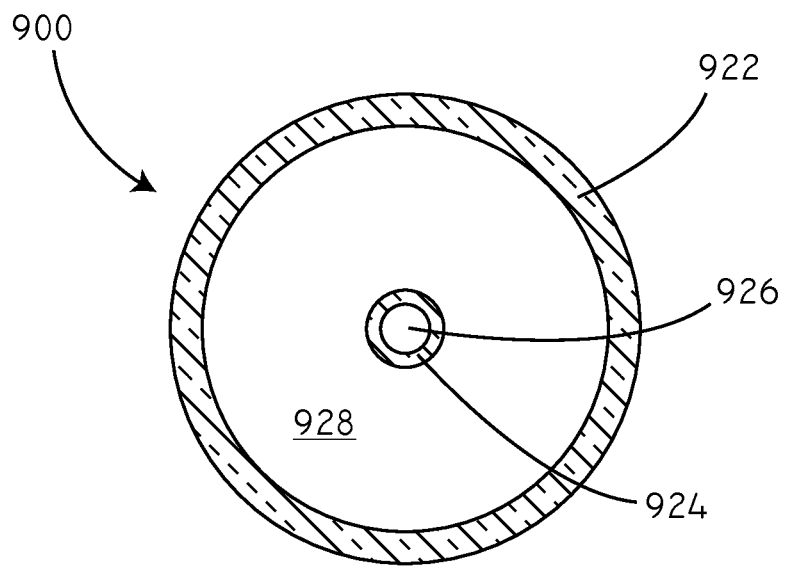
FIG. 9 is a cross-sectional schematic view of a spacing element in accordance with various embodiments herein.

In some embodiments, the spacing elements can define a volume that can be filled with another components, can be inflated with air or a liquid, or that can be used to retain absorbed exudate (for example, as a fluid sequestering agent), and/or and antimicrobial agent. In some embodiments, the interior of the spacing elements is hollow. Referring now to FIG. 9, a cross-sectional schematic view of a spacing element 900 in accordance with various embodiments herein is shown. The spacing element 900 can include an outer layer 922 and an inner layer 924 that are separate from one another in cross-section such that they define a volume 928. The inner layer 924 can define a central lumen 926. In some embodiments, the outer layer 922 can include a material with elastomeric properties (for example, but not limited to, polyurethane) such that it can expand in size in response to the volume being filled with a fluid (such as air or a liquid) or other matter (such as a dispersion).

Figure 10:
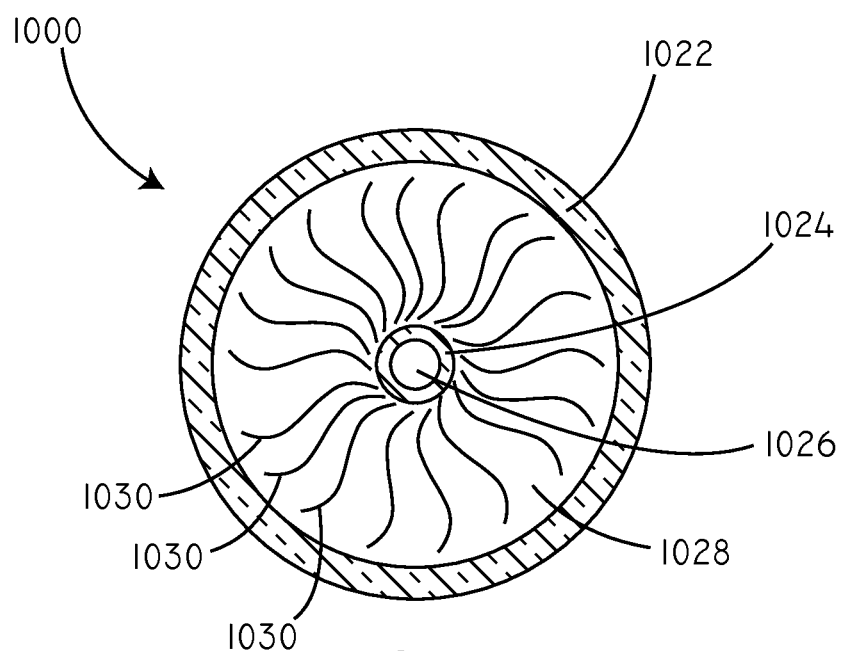
FIG. 10 is a cross-sectional schematic view of a spacing element in accordance with various embodiments herein.

In some embodiments, the spacing element can define a volume that can be filled with a material that aids in absorbing exudate. Referring now to FIG. 10, a cross-sectional schematic view of a spacing element 1000 in accordance with various embodiments herein is shown. The spacing element 1000 can include an outer layer 1022 and an inner layer 1024 that are separate from one another in cross-section such that they define a volume 1028. The inner layer 1024 can define a central lumen 1026. In this embodiment, a plurality of hollow fibers 1030 are disposed within the volume 1028. In some embodiments, the hollow fibers can be a polysulfone polymer.

Figure 11:
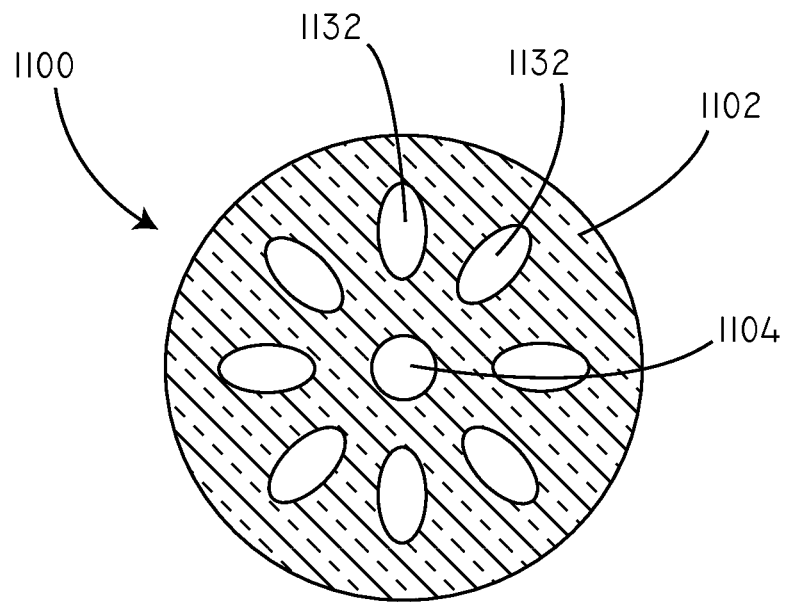
FIG. 11 is a cross-sectional schematic view of a spacing element in accordance with various embodiments herein.

In some embodiments, the spacing elements can include one or more interior volumes other than the central lumen. Referring now to FIG. 11 a cross-sectional schematic view of a spacing element 1100 is shown in accordance with various embodiments herein. The spacing element 1100 is shown including a portion 1102 surrounding a central lumen 1104. The spacing element 1100 can further include a plurality of interior volumes 1132 that can be used to store exudate or can be filled with another material.

In addition, various other elements can be disposed within spacing elements. By way of example, in some embodiments a radio frequency identification device (RFID) can be disposed within a spacing element. In some embodiments a metal, such as a ferrous metal, can be disposed within a spacing element. In some embodiments a radiopaque material can be disposed within a spacing element. These exemplary elements, disposed within spacing elements, can be useful for detection and/or retrieval of wound packing devices from wounds.

Figure 12:
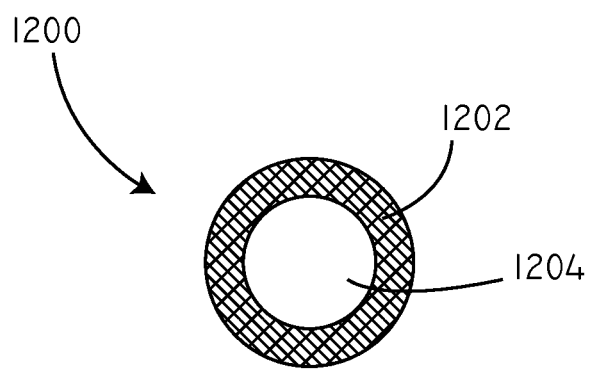
FIG. 12 is a cross-sectional schematic view of a connector in accordance with various embodiments herein.

Referring now to FIG. 12, a cross-sectional schematic view of a connector 1200 is shown in accordance with various embodiments herein. The connector 1200 can include a wall member 1202. The wall member 1202 can define a central lumen 1204. However, in other embodiments, the connector 1200 is solid in cross-sectional. In some embodiments, a material can be disposed within the lumen of the connector.

Figure 13:
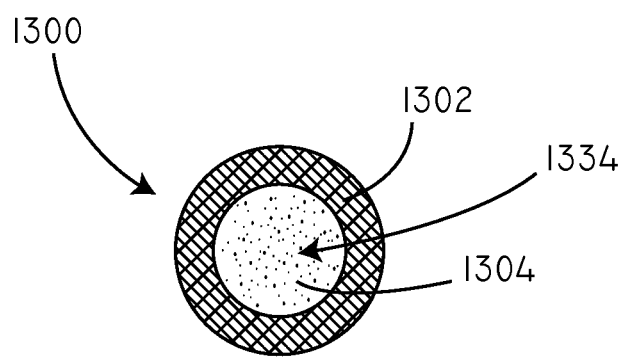
FIG. 13 is a cross-sectional schematic view of a connector in accordance with various embodiments herein.

Referring now to FIG. 13, a cross-sectional schematic view of a connector 1300 in accordance with various embodiments herein. The connector 1300 can include a wall member 1302 defining a central lumen 1304. A material 1334 can be disposed within the lumen 1304. By way of example, the material 1334 can include absorbent materials. In some embodiments the material 1334 can include superabsorbent materials. In some embodiments, calcium chloride can be disposed within the lumen 1304.

In some embodiments, the connector can be in fluid communication with one or more of the spacing elements such that fluid from one or more spacing elements can be transferred to the connector. In some embodiments the lumen of the connector is accessible from an end of the connector providing fluid communication between one or more of the spacing elements and the end of the connector. Exemplary fluid communication can provide for a negative pressure, or a suction, to remove exudate from the wound. Additionally, the wound can be covered, for example, with an adhesive film, such as a transparent dressing (TEGADERM™ Dressing, available from 3M Company, St. Paul, Minn.) to impart negative pressure over the entire aspect of the wound, and not just on the wound exudate.

Other embodiments can include applying a gas-impermeable wound dressing barrier over the wound and wound packing device. The method can further include regulating the negative pressure applied to the wound bed via the connector(s) and/or spacer(s) and for the degree of exudate removal achieved. The magnitude of negative pressure applied can also be further optimized for a particular tissue response and wound healing.

In yet other embodiments, the method can include putting a wound dressing that is a gas-permeable sterile barrier over the wound and previously placed wound packing device. The method can further include regulating the magnitude of vacuum or negative pressure applied to the connector(s) and spacer(s). In this example, the resulting pressure throughout the wound bed will be essentially atmospheric pressure or slightly less, and the degree of exudate removal may be independently controlled and optimized.

Figure 14:
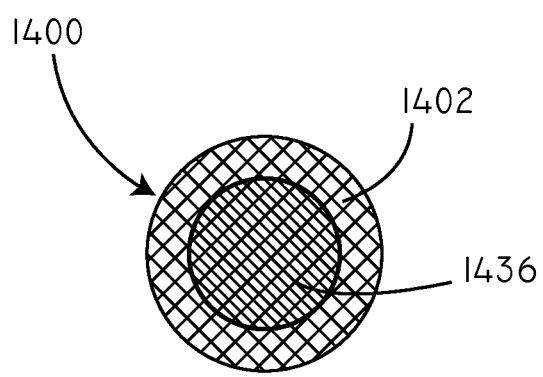
FIG. 14 is a cross-sectional schematic view of a connector in accordance with various embodiments herein.

In some embodiments, the connector can include a core and a layer of a material disposed over the core. Referring now to FIG. 14, a cross-sectional schematic view is shown of a connector 1400 in accordance with various embodiments herein. The connector 1400 can include a core 1436 and a layer 1402 disposed over the core 1436. In some embodiments, layer 1402 is a porous sleeve. In some embodiments layer 1402 can include a lubricious coating. In some embodiments layer 1402 can include a layer of flash-spun high-density polyethylene fibers. In some embodiments layer 1402 can include a layer of polytetrafluoroethylene (PTFE).

Figure 15:
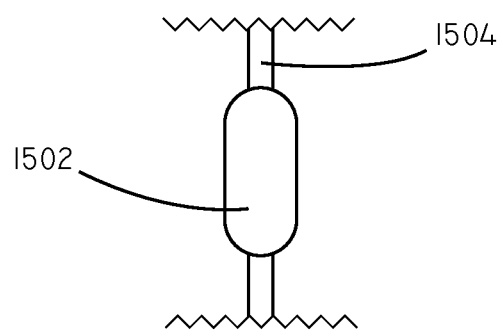
FIG. 15 is a schematic view of a spacing element in accordance with various embodiments herein.
Figure 16:
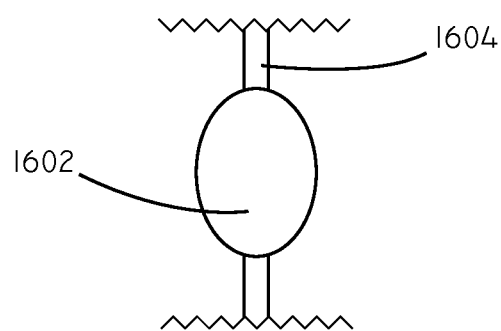
FIG. 16 is a schematic view of a spacing element in accordance with various embodiments herein.

It will be appreciated that spacing elements in accordance with embodiments herein can take on various shapes and sizes. By way of example, the spacing elements can be spherical, ovoid, toroidal, cubic, or the like. Referring now to FIG. 15, a schematic view is shown of a spacing element 1502 in accordance with various embodiments herein. The spacing element is shown attached to a connector 1504. Referring now to FIG. 16, a schematic view is shown of a spacing element 1602 in accordance with various embodiments herein. In this view, the spacing element 1602 is shown attached to a connector 1604.

Figure 17:
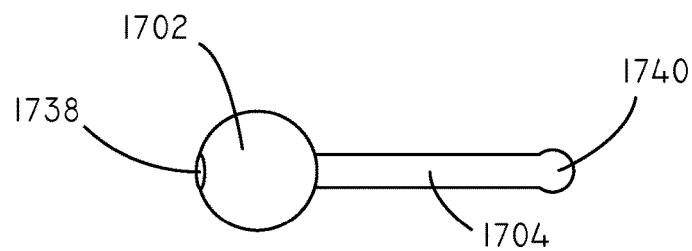
FIG. 17 is a schematic view of a connector segment and a spacing element in accordance with various embodiments herein.

Referring now to FIG. 17, a schematic view is shown of a connector 1704 and spacing element 1702 in accordance with various embodiments herein. The spacing element can include an aperture 1738. An end portion 1740 of the connector 1704 can fit within the aperture 1738 of an adjacent spacing element. In some embodiments, the end portion of a connector segment can be retained within the aperture of an adjacent spacing element. By way of example, a friction-fit retention mechanism can be used to retain the end portion of the connector segment within the aperture. In this manner, multiple connector segment and spacing element pairs can be attached together to form a wound packing device.

Figure 18:
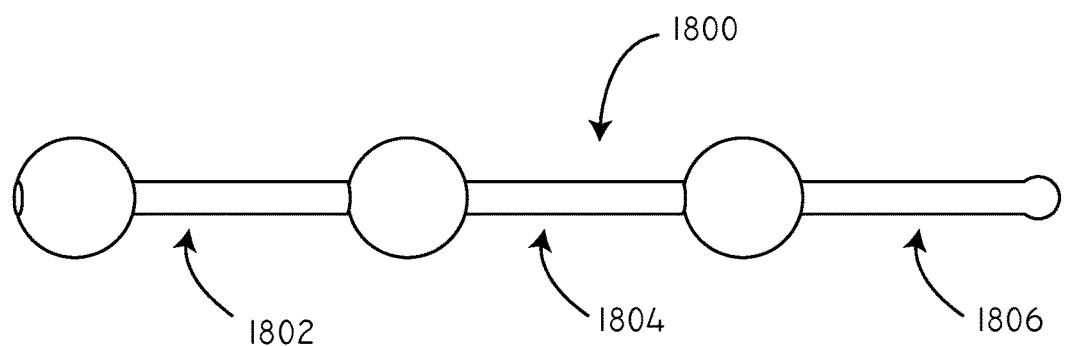
FIG. 18 is a schematic view of connector segments and spacing elements attached to one another in accordance with various embodiments herein.

Referring now to FIG. 18, a schematic view is shown of connector segments and spacing elements attached to one another to form a wound packing device 1800 in accordance with various embodiments herein. This embodiment can allow for customization of size of the wound packing device 1800. In specific, a first connector segment and spacing element pair 1802 is attached to a second connector segment and spacing element pair 1804, which it turn is attached to another connector segment and spacing element pair 1806. In actual use, any desired number of connector segment and spacing element pairs can be attached together. For example, in some embodiments from three to sixty pairs can be attached together.

Figure 19:
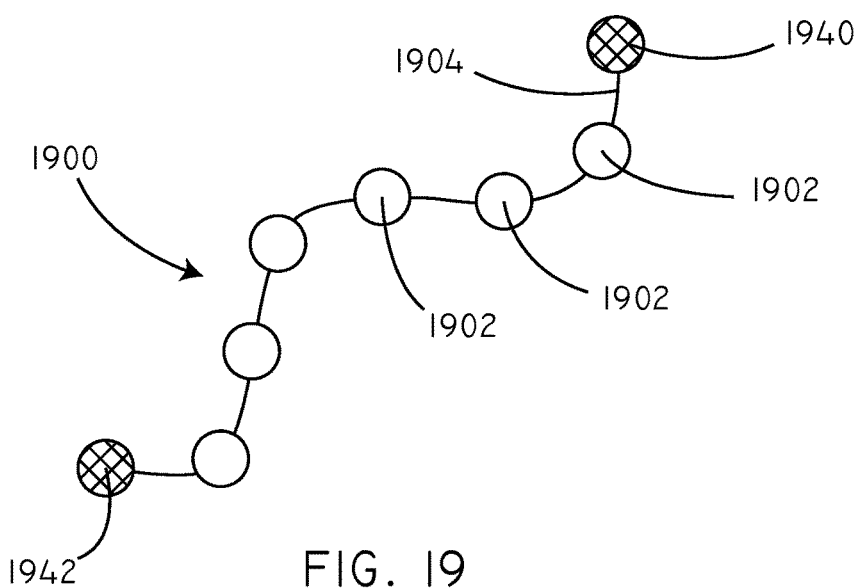
FIG. 19 is a schematic view of a wound packing device in accordance with various embodiments of the invention.

In some embodiments, indicia can be disposed on portions of the wound packing device. By way of example, indicia, such as specific coloration, letters, numbers, embossed surface characterizations, or combinations thereof can be disposed on spacing elements. Such indicia can be useful for various purposes. The indicia can allow an end user to more easily track the number of spacing elements being used, or to more quickly identify a default number of spacing elements by sight and/or feel. For example, every $10^{th}$ spacing element can be a different color in some embodiments. In some embodiments, a material can be used to form color on the spacing element that will change with time so as to indicate to a user when the device should be exchanged for a new device. In some embodiments, the color is configured to change with time. In some embodiments, the color is configured to change with the amount of exudate absorbed. Referring now to FIG. 19, a schematic view is shown of a wound packing device 1900 in accordance with various embodiments herein. The wound packing device 1900 includes a plurality of spacing elements 1902 attached together with a connector 1904. The wound packing device 1900 can also include a first colored spacing element 1940 and a second colored spacing element 1942. In some embodiments, the first colored spacing element 1940, second colored spacing element 1942, and other spacing elements 1902 are all different colors. In some embodiments, the first colored spacing element 1940 and the second colored spacing element 1942 are the same color. In yet other embodiments the first colored spacing element 1940 and second colored spacing element 1942 can have an embossed surface, whereas other spacing elements 1902 can have a smooth surface.

Figure 20:
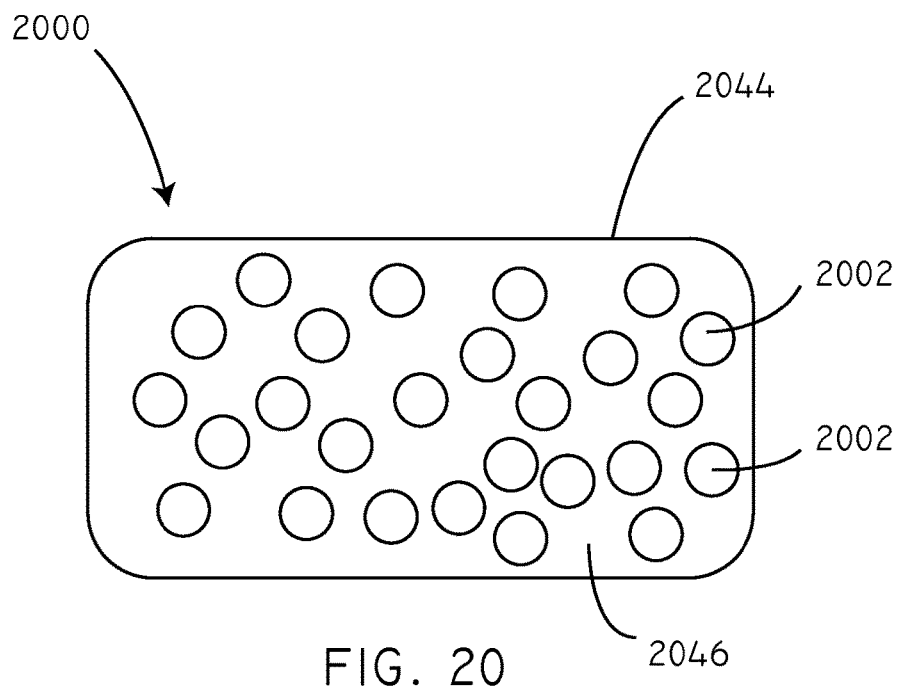
FIG. 20 is a schematic view of a plurality of spacing elements disposed within a container in accordance with various embodiments of the invention.

In some embodiments, spacing elements can be disposed together within a container, such as a bag, to form a wound packing device. Referring now to FIG. 20, a schematic view is shown of wound packing device 2000 including a plurality of spacing elements 2002 disposed within a container 2044. In some embodiments the container 2044 can be a water permeable bag. The container can enclose a space 2046 and the spacing elements 2002 can be within the space 2046. In some embodiments, the spacing elements 2002 can be attached to one another with a connector. In other embodiments, the connector can be absent.

Figure 21:
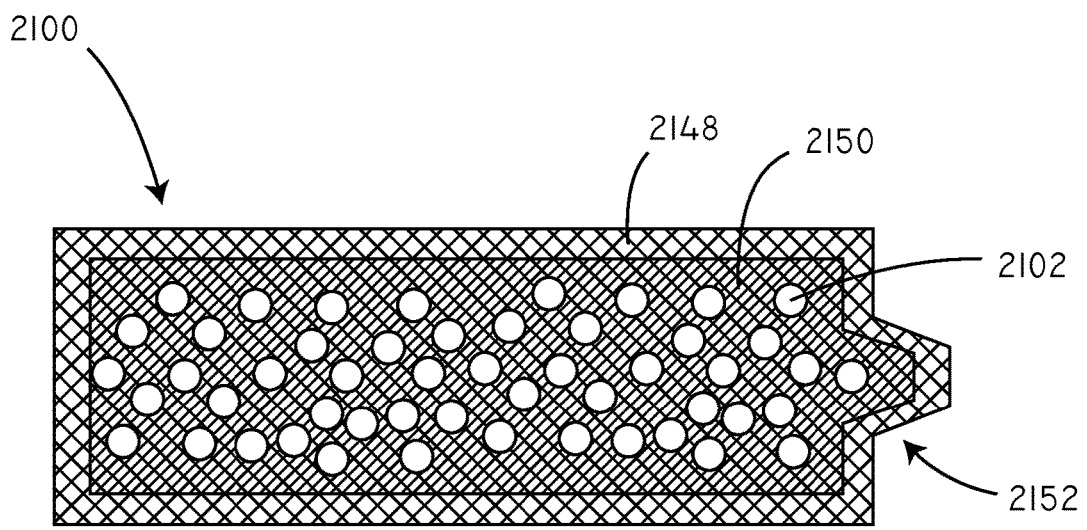
FIG. 21 is a schematic view of a plurality of spacing elements disposed with a packing material inside of a container in accordance with various embodiments of the invention.

In some embodiments, other materials can be packed along with the spacing elements and/or connector. By way of example, in some embodiments, the spacing elements can be packed with a paste inside of a bag or container. In some embodiments, the spacing elements are removed from the container before insertion into a wound bed, in other embodiments the spacing elements stay in the container and the combination is inserted into the wound bed. Referring now to FIG. 21, a schematic view is shown of a wound packing device 2100 including plurality of spacing elements 2102 disposed with a packing material 2150 inside of a container 2148. In some embodiments, the container 2148 can include an egress neck 2152 which can be opened to form an orifice through which the materials can be dispensed out of the container 2148 and into a wound bed. In yet other embodiments the egress neck 2152 can be an extended cannula through which the wound packing device 2100 can be delivered into a deep wound or fistula.

Figure 22:
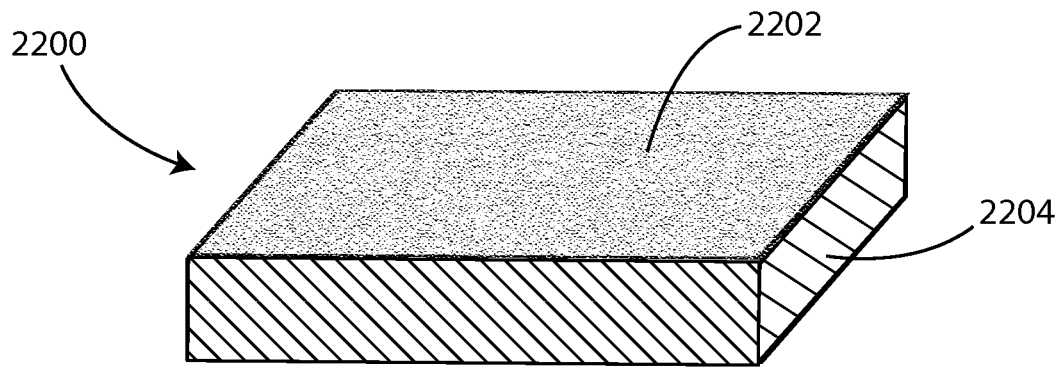
FIG. 22 is a schematic cross-sectional view of a portion of a device in accordance with various embodiments herein.

As previously described, various embodiments here include nanotextured surfaces. Referring now to FIG. 22, a schematic cross-sectional view is shown of a portion 2200 of a device in accordance with various embodiments herein. The portion 2200 of the device shown can include a surface 2202 that is nanotextured. The portion 2200 shown can include a core portion of material 2204 (or substrate) that can be effective to absorb exudate. In other embodiments, the core portion of material 2204 may be made from a material that does not absorb exudate. In some embodiments, the core portion of material 2204 is swellable. In some embodiments, the core portion of material 2204 is non-swellable. In some embodiments, core portion of material 2204 can be comprised of a porous material. In some embodiments, the core portion of material 2204 can be comprised of a non-porous material. In some embodiments, core portion of material 2204 includes a fluid sequestering material. In some embodiments, core portion of material 2204 forms part of a spacing element.

Figure 23:
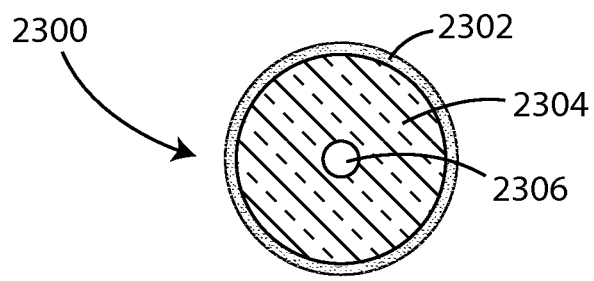
FIG. 23 is a schematic cross-sectional view of a spacing element in accordance with various embodiments herein.

Referring now to FIG. 23 is a schematic cross-sectional view of a spacing element 2300 in accordance with various embodiments herein. The spacing element 2300 can include a nanotextured surface 2302 and a core portion of material 2304. The spacing element 2300 can define a central channel or lumen 2306. The connector (not shown in this view) can pass through the lumen 2306.

Figure 24:
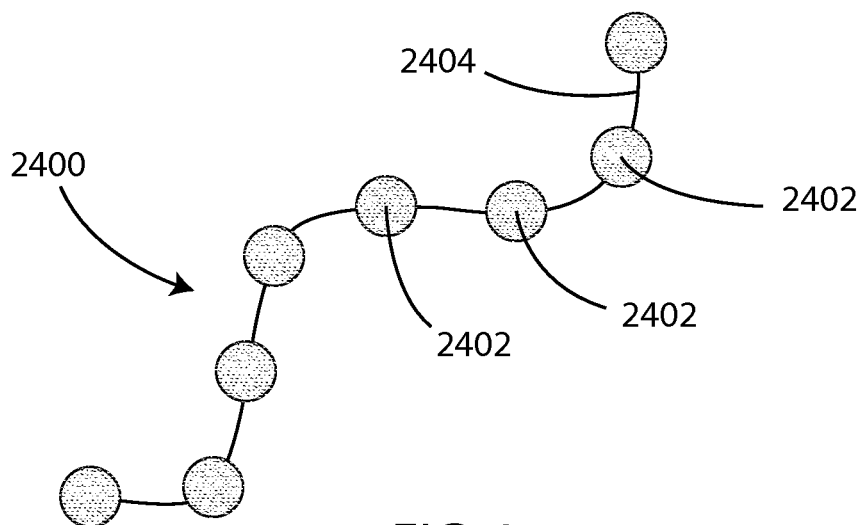
FIG. 24 is a schematic view of a wound packing device in accordance with various embodiments of the invention.

FIG. 24 is a schematic view of a wound packing device 2400 in accordance with various embodiments of the invention. The wound packing device 2400 includes a plurality of spacing elements 2402 attached together with a connector 2404. The surface of the spacing elements 2402 can be nanotextured.

In some embodiments, wound packing kits are included. By way of example, kits can include a plurality of spacing elements, the spacing elements comprising a nanotextured surface, the plurality of spacing elements configured to absorb exudate. The kits can also include a connector for connecting the plurality of spacing elements to one another. The connector comprising a fitting to allow for the number of spacing elements connected to one another by the connector to be modified by an end user.

Methods

In some embodiments, a method of making a wound packing device is included. The method can include forming a plurality of spacing elements. It will be appreciated that are many different techniques that can be used to form spacing elements in accordance with embodiments herein. In some embodiments, the spacing elements can be molded, sprayed, dipped, and the like. In some cases, depending on the polymers used, the composition will also include a solvent. In other embodiments, the composition can be solventless before forming into a spacing element. In some embodiments, manufacturing can include a number of steps. For example, the inner region or core of the spacing element can be formed in a first operation and then a layer of material can be disposed on top of the inner region. The method can also include an operation of mounting a plurality of spacing elements on a connector. Mounting can include forming the spacing elements in place on the connector. Mounting can also include threading the spacing elements onto the connector. In some embodiments, an adhesive can be used to retain the spacing elements in place on the connector. In other embodiments, spacing elements can be retained in place through a friction fit. In some embodiments, the method can include an operation of inflating the spacing elements.

In some embodiments, a method of treating wounds is included. The method can include dispensing a wound packing device from a sterile package. In some embodiments, dispensing can include removing a portion of spacing elements from a multi-segment package, such that other portions remain unopened and sterile. In some embodiments, dispensing can include counting the number of spacing elements. In some embodiments dispensing can include cutting the connector, or otherwise separating a portion of the connector, in order to prepare a desired number of spacing elements for insertion into a wound bed. The method can further include inserting the wound packing device into a wound bed. In some embodiments, the method can further include putting a wound dressing over the wound packing device. In some embodiments, the method can also include attaching a vacuum system (or another device that can generate a negative air pressure) to the wound packing device. By way of example, a vacuum system can be put in fluid communication with the connector, which can transfer exudate away from the spacing devices.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A wound packing device comprising:
   a plurality of spacing elements, the spacing elements comprising a nanotextured surface, the nanotextured surface exhibiting nanometer scale surface roughness;
   a connector connecting the plurality of spacing elements to one another;
   wherein the plurality of spacing elements and the connector are capable of absorbing exudate; and
   wherein the connector comprises a lumen, and wherein the lumen of the connector is in fluid communication with one or more of the spacing elements such that fluid from the one or more spacing elements can be transferred to the lumen of the connector.

2. The wound packing device of claim 1, wherein the lumen of the connector is accessible from an end of the connector providing fluid communication between one or more of the spacing elements and the end of the connector.

3. A wound packing device comprising:
- a plurality of spacing elements, the spacing elements comprising a nanotextured surface;
- a container, the plurality of spacing elements disposed within the container;
  - the container comprising an egress neck that can be opened to form an orifice through which the spacing elements can be dispensed; and
- a packing material disposed inside of the container.

4. The wound packing device of claim 3, the egress neck comprising an extended cannula through which the wound packing device can be delivered into a deep wound or fistula.

* * * * *